United States Patent
Armes et al.

(10) Patent No.: US 9,719,132 B2
(45) Date of Patent: *Aug. 1, 2017

(54) MONITORING RECOMBINASE POLYMERASE AMPLIFICATION MIXTURES

(71) Applicant: ALERE SAN DIEGO, INC., San Diego, CA (US)

(72) Inventors: Niall A. Armes, Helions Bumpstead (GB); Olaf Piepenburg, Saffron Walden (GB); Catherine Jean Greenwood, Sawbridgeworth (GB)

(73) Assignee: Alere San Diego Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/841,203

(22) Filed: Aug. 31, 2015

(65) Prior Publication Data

US 2016/0068898 A1    Mar. 10, 2016

Related U.S. Application Data

(63) Continuation of application No. 14/183,113, filed on Feb. 18, 2014, now Pat. No. 9,157,127, which is a continuation of application No. 13/441,411, filed on Apr. 6, 2012, now Pat. No. 8,809,021.

(60) Provisional application No. 61/472,919, filed on Apr. 7, 2011.

(51) Int. Cl.
*C12Q 1/68* (2006.01)
*G01N 21/64* (2006.01)

(52) U.S. Cl.
CPC .......... *C12Q 1/6851* (2013.01); *C12Q 1/689* (2013.01); *C12Q 1/6844* (2013.01); *G01N 21/6428* (2013.01); *G01N 21/6456* (2013.01); *C12Q 2600/158* (2013.01); *G01N 2021/6432* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,965,188 A | 10/1990 | Mullis et al. |
| 5,223,414 A | 6/1993 | Zarling et al. |
| 5,273,881 A | 12/1993 | Sena et al. |
| 5,326,692 A | 7/1994 | Brinkley et al. |
| 5,418,149 A | 5/1995 | Gelfand et al. |
| 5,536,649 A | 7/1996 | Fraiser et al. |
| 5,656,430 A | 8/1997 | Chirikjian |
| 5,665,572 A | 9/1997 | Ikeda et al. |
| 5,670,316 A | 9/1997 | Sena et al. |
| 5,792,607 A | 8/1998 | Backman et al. |
| 5,849,547 A | 12/1998 | Cleuziat |
| 5,858,652 A | 1/1999 | Laffler et al. |
| 6,087,112 A | 7/2000 | Dale |
| 6,251,600 B1 | 6/2001 | Winger et al. |
| 6,379,899 B1 | 4/2002 | Ullmann |
| 6,387,621 B1 | 5/2002 | Wittwer |
| 6,699,693 B1 | 3/2004 | Marians et al. |
| 6,929,915 B2 | 8/2005 | Benkovic et al. |
| 7,252,940 B2 | 8/2007 | Kutyavin et al. |
| 7,270,981 B2 | 9/2007 | Armes et al. |
| 7,282,328 B2 | 10/2007 | Kong |
| 7,399,590 B2 | 7/2008 | Piepenburg et al. |
| 7,435,561 B2 | 10/2008 | Piepenburg et al. |
| 7,666,598 B2 | 2/2010 | Piepenburg et al. |
| 8,062,850 B2 | 11/2011 | Piepenburg et al. |
| 2001/0044111 A1 | 11/2001 | Carr et al. |
| 2002/0061530 A1 | 5/2002 | Belotserkovskii et al. |
| 2002/0155573 A1 | 10/2002 | Lanes et al. |
| 2003/0108936 A1 | 6/2003 | Wagner |
| 2003/0143525 A1 | 7/2003 | Benkovic et al. |
| 2003/0219792 A1 | 11/2003 | Armes et al. |
| 2003/0228611 A1 | 12/2003 | Chruch et al. |
| 2004/0101893 A1 | 5/2004 | Kutyavin et al. |
| 2004/0137456 A1 | 7/2004 | Yokota et al. |
| 2004/0224336 A1 | 11/2004 | Wagner |
| 2005/0059003 A1 | 3/2005 | Enoki et al. |
| 2005/0112631 A1 | 5/2005 | Piepenburg et al. |
| 2005/0136443 A1 | 6/2005 | Shigemori |
| 2006/0110765 A1 | 5/2006 | Wang |
| 2007/0054296 A1 | 3/2007 | Piepenburg |
| 2007/0154914 A1 | 7/2007 | Gelfand et al. |
| 2007/0265198 A1 | 11/2007 | Fischetti et al. |

(Continued)

FOREIGN PATENT DOCUMENTS

| | | |
|---|---|---|
| CA | 2476481 | 9/2003 |
| EP | 0 624 643 | 4/1994 |

(Continued)

OTHER PUBLICATIONS

Accession: NP_861734 [GI: 32453528], Definition: UvsX RecA—like recombination protein [Enterobacteria phage RB69]. NCBI Sequence Revision History [online]; Mar. 30, 2006 uploaded, NCBI, <URL: http://www.ncbi.nlm.nih.gov/protein/32453528?sat=12&satkey=7706006> [retrieved on Aug. 30, 2011].
Accession: NP_861890 [GI: 32453681], Definition: UvsY recombination, repair and ssDNA binding protein [Enterobacteria phage RB69]. NCBI Sequence Revision History [online]; Mar. 30, 2006 uploaded, NCBI, <URL: http://www.ncbi.nlm.nih.gov/protein/32453681?sat=12&satkey=7706006> [retrieved on Aug. 30, 2011].
Adams et al., "Dissociation of RecA filaments from duplex DNA by the RuvA and RuvB DNA repair proteins," Proc. Natl. Acad. Sci. USA 91:9901-9905, 1994.

(Continued)

*Primary Examiner* — Anand Desai
(74) *Attorney, Agent, or Firm* — Fish & Richardson P.C.

(57) ABSTRACT

A process includes providing a mixture that includes a recombinase, a single-strand binding protein, and one or more oligonucleotides; and detecting particles in the reaction mixture.

19 Claims, 16 Drawing Sheets
(13 of 16 Drawing Sheet(s) Filed in Color)

(56) References Cited

U.S. PATENT DOCUMENTS

| | | | |
|---|---|---|---|
| 2008/0293045 A1 | 11/2008 | Piepenburg et al. | |
| 2009/0017462 A1 | 1/2009 | Piepenburg et al. | |
| 2009/0029421 A1 | 1/2009 | Piepenburg et al. | |
| 2010/0311127 A1 | 12/2010 | Piepenburg | |

FOREIGN PATENT DOCUMENTS

| | | |
|---|---|---|
| EP | 0 702 090 | 3/1996 |
| EP | 0 810 436 | 12/1997 |
| EP | 1118658 | 7/2001 |
| EP | 1 420 069 | 5/2004 |
| EP | 1 564 306 | 8/2005 |
| JP | 2008-500831 | 1/2008 |
| WO | WO 91/17267 | 11/1991 |
| WO | WO 93/05178 | 3/1993 |
| WO | WO 97/20078 | 6/1997 |
| WO | WO 98/08975 | 3/1998 |
| WO | WO 00/41524 | 7/2000 |
| WO | WO 02/086167 | 10/2002 |
| WO | WO 03/027640 | 4/2003 |
| WO | WO 03/038053 | 5/2003 |
| WO | WO 03/072805 | 9/2003 |
| WO | WO 2004/007078 | 1/2004 |
| WO | WO 2004/027025 | 4/2004 |
| WO | WO 2005/118853 | 12/2005 |
| WO | WO 2007/096702 | 8/2007 |
| WO | WO 2008/035205 | 3/2008 |
| WO | WO 2009/105648 | 8/2009 |
| WO | WO 2010/141940 | 12/2010 |

OTHER PUBLICATIONS

Alexseyev et al., "Genetic Characteristics of New recA Mutants of Escherichia coli K-12," J. Bacteriol., 178:2018-2024, 1996.

Amasino, "Acceleration of Nucleic Acid Hybridization Rate by Polyethylene Glycol," Anal. Biochem., 152:304-307, 1986.

Bains and Smith, "A Novel Method for Nucleic Acid Sequence Determination," J. Theor. Biol., 135:303-307, 1988.

Bar-Ziv and Libchaber, "Effects of DNA sequence and structure on binding of RecA to single-stranded DNA," PNAS USA, 98(16):9068-9073.

Baumann et al., "Purification of human Rad51 protein by selective spermidine precipitation," Mutat. Res., 384:65-72, 1997.

Benedict and Kowalczykowski, "Increase of the DNA Strand Assimiliation Activity of recA Protein by Removal of the C Terminus and Structure-Function Studies of the Resulting Protein Fragment," J. Biol. Chem., 263(30):15513-15520, 1988.

Benkovic et al., "Replisome-Mediated DNA Replication," Annu. Rev. Biochem., 70:181-208, 2001.

Bennett and Holloman, "A RecA Homologue in Ustilago maydis That Is Distinct and Evolutionarily Distant from Rad51 Actively Promotes DNA Pairing Reactions in the Absence of Auxiliary Factors," Biochemistry, 40:2942-2953, 2001.

Better and Helinski, "Isolation and Characterization of the recA Gene of Rhizobium meliloti," J. Bacteriol, 155:311-316, 1983.

Bianco and Weinstock, "Interaction of the RecA protein of Escherichia coli with single-stranded oligodeoxyribonucleotides," Nucleic Acids Research, 24(24):4933-4939, 1996.

Bianco et al., "DNA Strand Exchange Proteins: A Biochemical and Physical Comparison," Frontiers in Bioscience, oscience, 3:D570-D603, 1998.

Borjac-Natour et al., "Divergence of the mRNA targets for the Ssb proteins of bacteriophages T4 and RB69," Virology J., 1(4):1-14, 2004.

Bork et al., "The RecOR proteins modulate RecA protein function at 5' ends of single-stranded DNA," EMBO J., 20:7313-7322, 2001.

Bork et al., "RecA Protein Filaments Disassemble in the 5' to 3' Direction on Single-stranded DNA," J. Biol. Chem., 276:45740-45743, 2001.

Butler et al., "Investigating Structural Changes Induced by nucleotide Binding to RecA Using Difference FTIR," Biophysical J., 82(4):2198-2210, 2002.

Byrd and Raney, "Protein displacement by an assembly of helicase molecules aligned along single-stranded DNA," Nat. Struct. Mol. Biol., 11(6):531-538, 2004.

Cai, "An inexpensive and simple nucleic acid dipstick for rapid pathogen detection," LAUR #05-9067 of Los Alamos National Laboratory, Aug. 22, 2006.

Chan et al., "Effects of Polyethylene Glycol on Reverse Transcriptase and Other polymerase Activities," Biochim. Biophys. Acta., 606(2):353-361, 1980.

Compton, "Nucleic acid sequence-based amplification," Nature, 350:91-92, 1991.

Conklin and Drake, "Isolation and Characterization of conditional Alleles of bacteriophage T4 Genes uvsX and uvsY," Genetics, 107:505-523, 1984.

Cox et al., "The importance of repairing stalled replication forks," Nature, 404:37-41, 2000.

Cox et al., "A Simple and Rapid Procedure for the Large Scale Purification of the recA protein of Escherichia coli," J. Biol. Chem., 256:4676-4678, 1981.

Cromie and Leach, "Control of Crossing Over," Mol. Cell., 6:815-826. 2000.

Decker et al., "In Vitro Initiation of DNA Replication in Simian Virus 40 Chromosomes," J. Biol. Chem., 262(22):10863-10872, 1987.

Demidov, "Rolling-circle amplification in DNA diagnostics: the power of simplicity," Expert Rev. Mol. Diagn., 2(6):89-95, 2002.

Digard et al., "The Extreme C Terminus of Herpes Simplex Virus DNA Polymerase Is Crucial for Functional Interaction with Processivity Factor UL42 and for Viral Replication," J. Virol., 67(1):398-406, 1993.

Dillingham and Kowalczykowski, "A Step Backward in Advancing DNA Replication: Rescue of Stalled Replication Forks by RecG," Mol. Cell., 8:734-736, 2001.

Dong et al., "A coupled complex of T4 DNA replication helicase (gp41) and polymerase (gp43) can perform rapid and processive DNA strand-displacement synthesis," Proc. Natl. Acad. Sci. USA, 93:14456-14461, 1996.

Drmanac, et al., "Sequencing of Megabase Plus DNA by Hybridization: Theory of the Method," Genomics, 4:114-128, 1989.

Edwards et al., "Genetic Variation at Five Trimeric and Tetrameric Tandem Repeat Loci in Four Human Population Groups," Genomics, 12:241-253, 1992.

Eggler et al., "The C Terminus of the Escherichia coli RecA Protein Modulates the DNA Binding Competition with Single-stranded DNA-binding Protein," J. Biol. Chem., 278:16389-16396, 2003.

Eggleston and West, "Cleavage of Holliday Junctions by the Escherichia coli RuvABC Complex," J. Biol. Chem., 275:26467-26476, 2000.

Elias-Arnanz and Salas, "Bacteriophage ø29 DNA replication arrest caused by codirectional collisions with the transcription machinery," EMBO J., 16:5775-5783, 1997.

Ellis, "Macromolecular crowding: obvious but underappreciated," Trends in Biochem. Sci., 26(10):597-604, 2001.

Ellouze et al., "Evidence for elongation of the helical pitch of the RecA filament upon ATP and ADP binding using small-angle neutron scattering," Eur. J. Biochem., 23392):579-583, 1995.

Enright et al., The evolutionary history of methicillin-resistant Staphylococcus aureus (MRSA), Proc. Natl. Acad. Sci. USA, 99:7687-7692, 2002.

Fahy et al., "Self-sustained sequence replication (3SR): an isothermal transcription-based amplification system alternative to PCR," Genome Res, 1:25-33, 1991.

Ferrari et al., "Co-operative Binding of Escherichia Coli SSB Tetramers to Single-stranded DNA in the $(SSB)_{35}$ Binding Mode," J. Mol. Biol, 236:106-123, 1994.

Formosa et al., "Affinity purification of bacteriophage T4 proteins essential for DNA replication and genetic recombination," Proc. Natl. Acad. Sci. USA, 80:2442-2446, 1983.

Formosa and Alberts, "Purification and Characterization of the T4 Bacteriophage uvsX Protein," J. Biol. Chem., 261:6107-6118, 1986.

(56) References Cited

OTHER PUBLICATIONS

Formosa and Alberts, "DNA Synthesis Dependent on Genetic Recombination: Characterization of a Reaction Catalyzed by Purified Bacteriophage T4 Proteins," Cell, 47:793-806, 1986.
Fu et al., "Dynamics of DNA-tracking by two sliding-clamp proteins," EMBO J., 15(16):4414-4422, 1996.
Fuller et al., "Enzymatic replication of the origin of the *Escherichia coli* chromosome," Proc. Natl. Acad. Sci. USA, 78(12):7370-7374, 1981.
Giedroc et al., "The Function of Zinc in Gene 32 Protein from T4," Biochem., 26:5251-5259, 1987.
Giedroc et al., "Zn(II) Coordination Domain Mutants of T4 Gene 32 protein," Biochem., 31:765-774, 1992.
Ginocchio, "Life Beyond PCR: Alternative Target Amplification Technologies for the Diagnosis of Infectious Diseases, Part II," Clin. Microbiol. Newsletter, 26(17):129-136, 2004.
Glover and McHenry, "The DNA Polymerase III Holoenzyme: An Asymmetric Dimeric Replicative Complex with Leading and Lagging Strand Polymerases," Cell., 105:925-934.
Goodman et al., "Cloning and expression in *Escherichia coli* of a *recA*-like gene from *Bacteroides fragilis*," Gene, 58:265-271, 1987.
Hacker and Alberts, "Overexpression, Purification, Sequence Analysis, and Characterization of the T4 Bacteriophage dda DNA Helicase," J. Biol. Chem., 267:20674-20681, 1992.
Hammond et al., "Evaluation of 13 Short Tandem Repeat Loci for Use in Personal Identification Applications," Am. J. Hum. Genetics, 55:175-189, 1994.
Harris and Griffith, "UvsY Protein of Bacteriophage T4 is an Accessory Protein for in Vitro Catalysis of Strand Exchange," J. Mol. Biol., 206:19-27, 1989.
Harris and Griffith, "Visualization of the Homologous Pairing of DNA Catalyzed by the Bacteriophage T4 UvsX Protein," J. Biol. Chem., 262:9285-9292, 1987.
Harris and Griffith, "Formation of D Loops by the UvsX Protein of T4 Bacteriophage: A Comparison of the Reaction Catalyzed in the Presence or Absence of Gene 32 Protein," Biochem., 27:6954-6959, 1988.
Harvey et al., "Characterization and applications of CataCleave probe in real-time detection assays," Anal. Biochem., 333(2):246-255, 2004.
Heid et al., "Real time quantitative PCR," Genome Res., 6(10):986-994, 1996.
Heyer and Kolodner, "Purification and Characteirzation of a Protein from *Saccharomyces cerevisiae* That Binds Tightly to Single-Stranded DNA and Stimulates a cognate Strand Exchange Protein," Biochem. 28:2856-2862, 1989.
Hickson et al., "A Temperature Sensitive RecA Protein of *Escherichia coli*," Mol. Gen. Genet., 184:68-72, 1981.
Higashimoto et al., "Discriminating between Varicella-Zoster Virus Vaccine and Wild-Type Strains by Loop-Mediated Isothermal Amplification," J. Clin. Microbiol., 46(8):2665-2670, 2008.
Hopp et al., "A Short Polypeptide Marker Sequence Useful for Recombinant Protein Identification and Purification," Biotech., 6:1204-1210, 1988.
Hsieh et al., "The synapsis event in the homologous pairing of DNAs: RecA recognizes and pairs less than one helical repeat of DNA," Proc. Natl. Acad. Sci. USA, 89:6492-6496, 1992.
Huang et al., "Relationship between Bacteriophage T4 and T6 DNA Topoisomerases," J. Biol. Chem., 260(15):8973-8977, 1985.
Huletsky et al., "New Real-Time PCR Assay for Rapid Detection of Methicillin-Resistant *Staphylococcus aureus* Directly from Specimens Containing a Mixturre of *Staphylococci*," J. Clin. Microbiol., 42:1875-1884, 2004.
Ischenko and Saparbaev, "Alternative nucleotide incision repair pathway for oxidative DNA damage," Nature, 415(6868):183-187, 2002.
Ishmael et al., "Protein-Protein Interactions in the Bacteriophage T4 Replisome," J. Biol. Chem., 278(5):3145-3152, 2003.
Jarvis et al., "'Macromolecular Crowding': Thermodynamic Consequences for Protein-Protein Interactions with in the T4 DNA Replication Complex," J. Biol. Chem., 265(25):15160-15167, 1990.
Kaboord and Benkovic, "Rapid assembly of the bacteriophage T4 core replication complex on a linear primer/template construct," Proc. Natl. Acad. Sci. USA, 90:10881-10885, 1993.
Kaiser et al., "A Comparison of Eubacterial and Archaeal Structure-specific 5'-Exonucleases," J. Biol. Chem., 274(30):21387-21394, 1999.
Kato and Kuramitsu, "RecA Protein from an Extremely Thermophilic Bacterium, Thermus thermophiles HB8," J. Biochem., 114:926-929, 1993.
Katz and Bryant, "Interdependence of the Kinetics of NTP Hydrolysis and the Stability of the RecA-ssDNA Complex," Biochem., 40:11082-11089, 2001.
Kelman and O'Donnell, "DNA Polymerase III Holoenzyme: Structure and Function of a Chromosomal Replicating Machine," Annu. Rev. Biochem., 64:171-2000.
Khrapko et al., "An oligonucleotide hybridization approach to DNA sequencing," FEBS Lett., 256:118-122, 1989.
Komori et al., "Both RadA and RadB Are Involved in Homologous Recombination in *Pyrococcus furiosus*," J. Biol. Chem., 275:33782-33790, 2000.
Kool, "Replacing the Nucleobases in DNA with Designer Molecules," Acc. Chem. Res., 35:936-943, 2002.
Kowalczykowski et al., "Effects of the *Escherichia coli* SSB Protein on the Binding of *Escherichia coli* RecA Protein to Single-stranded DNA—Demonstration of Competitive Binding and the Lack of a Specific Protein-Protein Interaction," J. Mol. Biol., 193:81-95, 1987.
Kreader, "Relief of amplification inhibition in PCR with bovine serum albumin or T4 gene 32 protein," Appl. Env. Microbiol., 62:1102-1106, 1996.
Kuil et al., "The internal dynamics of gene 32 protein-DNA complexes studied by quasi-elastic light scattering," Biophys. Chem., 32:211-227, 1988.
Kuil et al., "A Refined Calculation of the Solution Dimensions of the Complex Between gene 32 Protein and Single Stranded DNA Based on Estimates of the Bending Persistence Length," J. Biomol. Struct. Dyn. 7(4):943-957, 1990.
Kuramitsu et al., "A Large-Scale Preparation and Some Physicochemical Properties of RecA Protein," J. Biochem., 90:1033-1045, 1981.
Kurumizaka et al., "A Chimeric RecA Protein Exhibits Altered Double-stranded DNA Binding," J. Biol. Chem., 269:3068-3075, 1994.
Lavery and Kowalczykowski, "Enhancement of recA Protein-promoted DNA Strand Exchange Activity by Volume-occupying Agents," J. Biol. Chem., 267:9301-9314, 1992.
Lavery and Kowalczykowski, "A Postsynaptic Role for Single-stranded DNA-binding Protein in recA Protein-promoted DNA Strand Exchange," J. Biol. Chem., 267(13):9315-9320, 1992.
LeBowitz and McMacken, "The bacteriophage λ O and P protein initiators promote the replication of single-stranded DNA," 12(7):1-20, 1984.
Lerman, "A Transition to a Compact Form of DNA in Polymer Solutions," Proc. Nat. Acad. Sci. USA, 68(8):1886-1890, 1971.
Levin et al., "Homogeneous *Escherichia coli* Endonuclease IV," J. Biol. Chem., 263:8066-8071, 1988.
Liu et al., "The Ordered Assembly of the øX174-type Primosome," J. Biol. Chem., 271:15656-15661, 1996.
Lohman and Ferrari, "*Escherichia coli* Single-Stranded DNA-Binding Protein: Multiple DNA-Binding Modes and Cooperativities," Annu. Rev. Biochem., 63:527-570, 1994.
Lovett and Roberts, "Purification of a RecA Protein Analogue from *Bacillus subtilis*," J. Biol. Chem., 260:3305-3313, 1985.
Lusetti et al., "Magnesium Ion-dependent Activation of the RecA Protein Involves the C Terminus," J. Biol. Chem., 278(18):16381-16388, 2003.
Lutz-Freyermuth et al., "Quantitative determination that one of two potential RNA-binding domains of the A protein component of the

(56) References Cited

OTHER PUBLICATIONS

U1 small nuclear ribonucleoprotein complex binds with high affinity to stem-loop II of U1 RNA," Proc. Natl. Acad. Sci. USA, 87:6393-6397, 1990.
Lysov et al., "Establishing Nucleotide Sequence of DNA using Oligonucleotide Hydridization. Novel Method," SSSR 303:1508-1511, 1988 (English translation).
Maeshima et al., "Purification and characterization of XRad51.1 protein, Xenopus RAD51 homologue: recombinant XRad51.1 promotes strand exchange reaction," Genes Cells, 1:1057-1068, 1996.
Maki et al., "DNA Polymerase III Holoenzyme of *Escherichia coli*," J. Biol. Chem., 263(14):6570-6578, 1988.
Malkov and Camerini-Otero, Photocross-links between Single-stranded DNA and *Escherichia coli* RecA Protein Map to Loops L1 (Amino Acid Residues 157-164) and L2 (Amino Acid Residues 195-209),: J. Biol. Chem., 270(50):30230-30233, 1995.
Marians, "Prokaryotic DNA Replication," Annu. Rev. Biochem., 61:673-719, 1992.
Marians, "PriA: At the Crossroads of DNA Replication and Recombination," Prog. Nucleic Acid Res. Mol. Biol., 63:39-67, 1999.
Marras et al., "Multiplex detection of single-nucleotide variations using molecular beacons," Genet. Anal. Biomolec. Eng., 14:151-156, 1999.
Martin et al., "GAP Domains Responsible for Ras p21-Dependent Inhibition of Muscarinic Atrial $K^{+C}$hannel Currents," Science, 255:192-194, 1992.
Maxam and Gilbert, "A new method for sequencing DNA," Proc. Natl. Acad. Sci. USA, 74:560-564, 1877.
Mazin and Kowalczykowski, "The function of the secondary DNA-binding site of RecA protein during DNA strand exchange," Proc. Natl. Acad. Sci. USA, 74:560-564, 1977.
McGlynn and Lloyd, "RecG helicase activity at three- and four-strand DNA structures," Nucl. Acid Res., 27:3049-3056, 1999.
McGlynn et al., "Characterisation of the catalytically active form of RecG helicase," Nucl. Acid Res., 28:2324-2332, 2000.
Minton, "The Influence of Macromolecular Crowding and Macromolecular Confinement on Biochemical Reactions in Physiological Media," J. Biol. Chem., 276(14):10577-10580, 2001.
Mitra and Church, "In situ localized amplification and contact replication of many individual DNA molecules," Nucl. Acids Res., 27(24):e34i-e34vi.
Mizuuchi, "In Vitro Transposition of Bacteriophage Mu: A Biochemical Approach to a Novel Replication Reaction," Cell, 35:785-794, 1983.
Morel et al., "Recombination-dependent Repair of DNA Double-strand Breaks with Purified Proteins from *Escherichia coli*," J. Biol. Chem., 272:17091-17096, 1997.
Morrical et al., "Amplification of Snap-back DNA Synthesis Reactions by the uvsX Recombinase of Bacteriophage T4," J. Biol. Chem., 266:14031-14038, 1991.
Morrical and Alberts, "The UvsY Protein of Bacteriophage T4 Modulates Recombination-dependent DNA Synthesis in Vitro," J. Biol. Chem., 265:15096-15103, 1990.
Morris and Raney, "DNA Helicases Displace Streptavidin from Biotin-Labeled Oligonucleotides," Biochem., 38(16):5164-5171, 1999.
Morrison et al., "Quantificationo f Low-Copy Transcripts by Continuous SYBR Green I Monitoring during Amplification," BioTechniques, 24:954-962, 1998.
Mosig et al., "Two recombination-dependent DNA replication pathways of bacteriophage T4, and their roles in mutagenesis and horizontal gene transfer," Proc. Natl. Acad. Sci. USA, 98:8306-8311, 2011.
Nadler et al., "A Novel Function for Zinc(II) in a Nucleic Acid-binding Protein," J. Biol. Chem., 265(18):10389-10394, 1990.
Nadeau et al., "Real-Time, Sequence-Specific Detection of Nucleic Acids during Strand Displacement Amplification," Anal. Biochem., 276(2):177-187, 1999.
Nagai et al., "Additive Effects of Bovine Serum Albumin, Dithiothreitol, and Glycerol in PCR," 44:157-163, 1998.

Naimushin et al., "Effect of Polyethylene Glycol on the Supercoiling Free Energy of DNA," Biopolymers, 58(2):204-217, 2001.
Ng and Marians, "The Ordered Assembly of the øX174-type Primosome," J. Biol. Chem., 271:15642-15648, 1996.
Ng and Marians, "The Ordered Assembly of the øX174-type Primosome," J. Biol. Chem., 271:15649-15655, 1996.
Okazaki and Kornberg, "Enzymatic Synthesis of Deoxyribonucleic Acid," J. Biol. Chem., 239:259-268, 1964.
Paulus and Bryant, "Time-Dependent Inhibition of recA Protein-Catalyzed ATPHydrolysis by ATPyS: Evidence for a Rate-Determining Isomerization of the recA-ssDNA Complex," Biochem., 36:7832-7838, 1997.
Petrov et al., "Plasticity of the Gene Functions for DNA Replication in the T4-like Phages," J. Mol. Biol., 361:46-68, 2006.
Pevzner, "1-Tuple DNA Sequencing: Computer Analysis," J. Biomol. Struct. Dyn., 7:63-73, 1989.
Pham et al., "A model for SOS-lesion-targeted mutations in *Escherichia coli*," Nature, 409:366-370, 2001.
Piepenburg et al., "DNA Detection Using Recombination Proteins," PLOS Biology, 4(7):1115-1121, 2006.
Pierre and Paoletti, "Purification and Characterization of recA Protein from *Salmonella typhimurium*," J. Biol. Chem., 258:2870-2874, 1983.
Podust et al., "Replication Factor C Disengages from Proliferating Cell Nuclear Antigen (PCNA) upon Sliding Clamp Formation, and PCNA Itself Tethers DNA Polymerase δ to DNA," J. Biol. Chem., 273(48):31992-31999, 1998.
Pomp and Medrano, "Organic Solvents as Facilitators of Polymerase chain Reaction," Biotechniques, 10(1):58-59, 1991.
Puthawibool et al., "Detection of shrimp infectious myonecrosis virus by reverse transcription loop-mediated isothermal amplification combined with a lateral flow dipstick," J. Virol. Methods, 156(1-2):27-31, 2009 (Abstract Only).
Qiu and Giedroc, "Effects of Substitution of Proposed Zn(II) Ligand $His^{81}$ or $His^{64}$ in Phage T4 Gene 32 Protein: Spectroscopic Evidence for a Novel Zinc Coordination Complex," Biochem., 33(26):8139-8148, 1994.
Raap, "Advances in fluorescence in situ hybridization," Mutation Research, 400:287-298, 1998.
Raap et al., "Synthesis and Proton-NMR Studies of Oligonucleotides Containing and Apurinic (AP) Site," J. Biom. Structure & Dynamics, 5(2):219-247, 1987.
Rashid et al., "RecA/Rad51 Homolog from *Thermococcus kodakaraensis* KOD1," Methods Enzymol., 334:261-270, 2001.
Reddy et al., "Assembly of a functional replication complex without ATP hydrolysis: A direct interaction of bacteriophage T4 gp45 with T4 DNA polymerase," Proc. Natl. Acad. Sci. USA, 90:3211-3215, 1993.
Reddy et al., "Using Macromolecular Crowding Agents to Identify Weak Interactions within DNA Replication Complexes," Methods Enzymol., 262:466-476, 1995.
Riddles and Lehman, "The Formation of Plectonemic Joints by the recA Protein of *Escherichia coli*," J. Biol. Chem., 260:170-173, 1985.
Rivas et al., "Life in a crowded world—Workshop on the Biological Implications of Macromolecular Crowding," EMBO Reports, 5(1):23-27, 2004.
Ronaghi et al., "A Sequencing Method Based on Real-Time Pyrophosphate," Science, 281:363-365, 1998.
Rosselli and Stasiak, "Energetics of RecA-mediated Recombination Reactions Without ATP Hydrolysis RecA Can Mediate Polar Strand Exchange But Is Unable to Recycle," J. Mol. Biol., 216:335-352, 1990.
Roux, "Optimization and troubleshooting in PCR," Genome Res., 4:S185-S194, 1995.
Saiki et al., "Primer-Directed Enzymatic Amplification of DNA with a Thermostable DNA Polymerase," Science, 239:487-491, 1988.
Salinas et al., "Homology Dependence of UvsX Protein-catalyzed Joint Molecule Formation," J. Biol. Chem., 270:5181-5186.
Salinas and Benkovic, "Characterization of bacteriophage T4-coordinated leading- and lagging-strand synthesis on a minicircle substrate," PNAS, 97(13):7196-7201, 2000.

(56) References Cited

OTHER PUBLICATIONS

Sanders et al., "Use of a macromolecular crowding agent to dissect interactions and define functions in transcriptional activation by a DNA-tracking protein: Bacteriphage T4 gene 45 protein and late transcription," Proc. Natl. Acad. Sci. USA, 91:7703-7707, 1994.
Sanders et al., "Dual targets of a transcriptional activator that tracks on DNA," EMBO J., 16(11):3124-3132, 1997.
Sanger et al., "DNA sequencing with chain-terminating inhibitors," Proc. Natl. Acad. Sci. USA, 75:5463-5467, 1977.
Savva and Pearl, "Cloning and Expression of the Uracil-DNA Glycosylase Inhibitor (UGI) From Bacteriophage PBS-1 and Crystallization of a Uracil-DNA Glycosylase-UGI Complex," Proteins, 22(3):287-289, 1995.
Scheerhagen et al., "Binding Stoichiometry of the Gene 32 Protein of Phage T4 in the Complex with Single Stranded DNA Deduced from Boundary Sedimentation," J. Biomol. Struct. Dyn., 3:887-898, 1986.
Scheerhagen et al., "Hydrodynamic studies of a DNA-protein complex—Dimensions of the complex of single-stranded 145 base DNA with gene 32 protein of phage T4 deduced from quasi-elastic light scattering," FEBS Lett., 184(2):221-225, 1985.
Shan et al., "RecA Protein Filaments: End-dependent Dissociation from ssDNA and Stabilization by RecO and RecR Proteins," J. Mol. Biol., 265:519-540, 1997.
Shibata et al., "Purified *Escherichia coli* recA protein catalyzes homologous pairing of superhelical DNA and single-stranded fragments," Proc. Natl. Acad. Sci. USA, 76:1638-1642, 1979.
Shibata et al., "Homologous pairing in genetic recombination: Formation of D loops by combined action of recA protein and a helix-destabilizing protein," Proc. Natl. Acad. Sci. USA, 77:2606-2610, 1980.
Shibata et al, "Homologous pairing in genetic recombination: Complexes of recA protein and DNA," Proc. Natl. Acad. Sci. USA, 76(10):5100-5104, 1979.
Singleton et al., "Structural Analysis of DNA Replication Fork Reversal by RecG," Cell, 107:79-89, 2001.
Skinner et al., "Use of the Glu-Glu-Phe C-terminal Epitope for Rapid Purification of the Catalytic Domain of Normal and Mutant *ras* GTPase-activating Proteins," J. Biol. Chem., 266:14163-14166, 1991.
Southern et al., "Analyzing and Comparing Nucleic Acid sequences by Hybridization to Arrays of Oligonucleotides: Evaluation Using Experimental Models," Genomics, 13:1008-1017, 1992.
Spies et al., "The RadA protein from a hyperthermophilic archaeon *Pyrobaculum islandicum* is a DNA-dependent ATPase that exhibits two disparate catalytic modes, with a transition temperature at 75° C," Eur. J. Biochem., 267:1125-1137, 2000.
Steffen and Bryant, "Purification and Characterization of the RecA Protein from *Streptococcus pneumoniae*," Arch. Biochem. Biophys., 382:303-309, 2000.
Story et al., "Structural Relationship of Bacterial RecA Proteins to Recombination Proteins from Bacteriophage T4 and Yeast," Science, 259(5103):1892-1896, 1993.
Sun and Shamoo, "Biochemical characterization of Interactions between DNA Polymerase and Single-stranded DNA-binding Protein in Bacteriophage RB69," J. Biol. Chem., 278(6):3876-3881.
Takeshita et al., "Oligodeoxynucleotides Containing Synthetic Abasic Sites," J. Biol. Chem., 262:10171-10179, 1987.
Tang et al., "Roles of *E. coli*DNA polymerases IV and V in lesion-targeted and untargeted SOS mutagenesis," Nature, 404:1014-1018, 2000.
Tinker-Kulberg et al., "A direct interaction between a DNA-tracking protein and a promoter recognition protein: implications for searching DNA sequence," EMBO J., 15(18):5032-5039, 1996.
Tissier et al., "Purification and Characterization of a DNA Strand Transferase from Broccoli," Plant Physiol., 108:379-386, 1995.
Tracy and Kowalczykowski, "In vitro selection of preferred DNA pairing sequences by the *Escherichia coli* RecA protein," Genes Dev., 10:1890-1903, 1996.

Tsurimoto and Matsubara, "Replication of λ dv plasmid in vitro promoted by purified λ O and P proteins," Proc. Natl. Acad. Sci. USA, 79:7639-7643, 1982.
Tyagi et al., "Multicolor molecular beacons for allele discrimination," Nature Biotechnol., 16:49-53, 1998.
Van Ness et al., "Isothermal reactions for the amplification of oligonucleotides," Proc. Natl. Acad. Sci. USA, 100(8):4504-4509, 2003.
Villemain et al., "Mutations in the N-terminal Cooperativity Domain of Gene 32 protein Alter Properties of the T4 DNA Replication and Recombination Systems," J. Biol. Chem., 275:31496-31504, 2000.
Vincent et al., "Helicase-dependent isothermal DNA amplification," EMBO Rep., 5:795-800, 2004.
Volodin and Camerini-Otero, "Influence of DNA Sequence on the Positioning of RecA Monomers in RecA-DNA Cofilaments," J. Biol. Chem., 277(2):1614-1618, 2002.
Volodin et al., "Phasing of RecA monomers on quasi-random DNA sequences," FEBS Letters, 546:203-208, 2003.
Voloshin et al., "Homologous DNA Pairing Promoted by a 20-Amino Acid Peptide Derived from RecA," Science, 272:868-872, 1996.
Voloshin et al., "The Homologous Pairing Domain of RecA also Mediates the Allosteric Regulation of DNA Binding and ATP Hydrolysis: A Remarkable Concentration of Functional Residues," J. Mol. Biol., 303(5):709-720, 2000.
Waidner, et al., "Domain effects on the DNA-interactive properties of bacteriophage T4 gene 32 protein," J. Biol. Chem., 276:2509-16 (2001).
Walker et al., "Isothermal in vitro amplification of DNA by a restriction enzyme/DNA polymerase system," Proc. Natl. Acad. Sci. USA, 89:392-396, 1992.
Walker, "Empirical aspects of strand displacement amplification," Genome Res., 3:1-6, 1993.
Walker et al., "Distantly related sequences in the α- and β-subunits of ATP synthase, myosin, kinases and other ATP-requiring enzymes and a common nucleotide binding fold," EMBO J., 1:945-951, 1982.
Wang et al., "Modular Organization of T4 DNA Polymerase," J. Biol. Chem., 270(44):26558-26564, 1995.
Wang and Mosbaugh, "Uracil-DNA Glycosylase Inhibitor of Bacteriophage PBS2: Cloning and Effects of Expression of the Inhibitor Gene in *Escherichia coli*," J. Bacteriol., 170(3):1082-1091, 1988.
Webb et al., "An Interaction between the *Escherichia coli* RecF and RecR Proteins Dependent on ATP and Double-stranded DNA," J. Biol. Chem., 270:31397-31404, 1995.
Webb et al., "Recombinational DNA Repair: The RecF and RecR Proteins Limit the Extension of RecA Filaments beyond Single-Strand DNA Gaps," Cell, 91:347-356, 1997.
Webb et al., "ATP Hydrolysis and DNA Binding by the *Escherichia coli* RecF Protein," J. Biol. Chem., 274:15367-15374, 1999.
West et al., "Purification and Properties of the recA Protein of *Proteus mirabilis*," J. Biol. Chem., 258:4648-4654, 1983.
Wetmur et al, "Cloning, Sequencing, and Expressiono f RecA Proteins from Three Distantly Related Thermophilic Eubacteria," J. Biol. Chem., 269:25928-25935, 1994.
Wittwer et al., "Continuous Fluorescence Monitoring of Rapid Cycle DNA Amplification," Biotechniques, 22(1):130-1, 134-138, 1997.
Xu and Marians, "A Dynamic RecA Filament Permits DNA Polymerase-catalyzed Extension of the Invading Strand in Recombination Intermediates," J. Biol. Chem., 277:14321-14328, 2002.
Yang et al., "Comparison of Bacteriophage T4 and UvsX and Human Rad51 Filaments Suggests that RecA-like Polymers May Have Evolved Independently," J. Mol. Biol., 312(5):999-1009, 2001.
Yeh et al., "Divergence of a DNA Replication Gene Cluster in the T4-Related Bacteriophage RB69," J. Bacteriol., 180(8):2005-2013, 1998.
Yonesaki et al., "Purification and some of the functions of the product of bacteriophage T4 recombination genes, *uvs*X and *uvs*Y ," Eur. J. Biochem., 148:127-134, 1985.

(56) References Cited

OTHER PUBLICATIONS

Young et al., "The Kinetic Mechanism of Formation of the Bacteriophage T4 DNA polymerase Sliding Clamp," J. Mol. Biol., 264:440-452, 1996.
Zhang et al., "Ramification Amplification: A Novel Isothermal DNA Amplification Method," Mol. Diagn., 6:141-150, 2001.
Zimmerman and Trach, "Macromolecular crowding extends the range of conditions under which DNA polymerase is functional," Biochim. Biophys. Acta., 949:297-304, 1988.
Zimmerman and Minton, "Macromolecular Crowding: Biochemical, Biophysical, and Physiological Consequences," Annu. Rev. Biophys. Biomol. Struct., 22:27-65, 1993.
Zimmerman and Harrison, "Macromolecular crowding increases binding of DNA polymerase to DNA: An adaptive effect," Proc. Natl. Acad. Sci. USA, 84(7):1871-1875, 1987.
Zinchenko and Yoshikawa, "$Na^+$ Shows a Markedly Higher Potential than $K^+$ in DNA Compaction in a Crowded Environment," Biophysical Journal, 88:4118-4123, 2005.
International Search Report and Written Opinion, for the corresponding PCT Application No. PCT/US2012/032508, dated Jul. 6, 2012.
Extended European Search Report in corresponding Application No. 12767452.1, dated Nov. 26, 2014, pp. 1-7.
Feng Shen et al., "Digital PCR on a SlipChip," Internet Citation, Jan. 1, 2010, pp. 1-10.
Office Action in corresponding Japanese Application No. 2014-504020, dated Feb. 2, 2016, pp. 1-6.

MONITORING RECOMBINASE POLYMERASE AMPLIFICATION MIXTURES

CROSS-REFERENCE TO RELATED APPLICATION

This application is a continuation and claims priority to U.S. patent application Ser. No. 14/183,113, filed Feb. 18, 2014, now U.S. Pat. No. 9,157,127, which is a continuation and claims priority to U.S. patent application Ser. No. 13/441,411, filed Apr. 6, 2012, now U.S. Pat. No. 8,809,021, which claims priority to U.S. Patent Application Ser. No. 61/472,929, filed Apr. 7, 2011, the entire contents of which are incorporated by reference.

TECHNICAL FIELD

This disclosure relates to methods and compositions for nucleic acid detection, amplification, and quantitation.

BACKGROUND

Certain isothermal amplification methods are able to amplify template (target) nucleic acid in a specific manner from trace levels to very high and detectable levels within a matter of minutes. Such isothermal methods, e.g., Recombinase Polymerase Amplification (RPA), can broaden the application of nucleic acid based diagnostics into emerging areas such as point-of-care testing, and field and consumer testing. The isothermal nature and broad temperature range of the technologies can allow users to avoid the use of complex power-demanding instrumentation.

SUMMARY

This disclosure is based, at least in part, on the observation of particles within RPA mixtures. In some embodiments, these particles can include nucleic acids (e.g., oligonucleotides) and/or protein components of the RPA reaction. This discovery provides for new monitoring and detection methods relating to RPA.

In one aspect, this disclosure features processes that include: (a) providing a mixture that includes one or more of (e.g., two or more, or all of) a recombinase, a single-stranded DNA binding protein, and one or more nucleic acids (e.g., oligonucleotides) (in any combination); and (b) detecting particles in the reaction mixture. In some embodiments, the mixture includes a crowding agent, e.g., one or more of polyethylene glycol (e.g., PEG1450, PEG3000, PEG8000, PEG10000, PEG14000, PEG15000, PEG20000, PEG250000, PEG30000, PEG35000, PEG40000, PEG compound with molecular weight between 15,000 and 20,000 daltons, or combinations thereof), polyvinyl alcohol, dextran and ficoll. In some embodiments, the crowding agent is present in the reaction mixture at a concentration between 1 to 12% by weight or by volume of the reaction mixture, e.g., between any two concentration values selected from 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, and 12.0%.

In some embodiments of all aspects, the recombinase includes a RecA or UvsX recombinase. In some embodiments of all aspects, the single-stranded DNA binding protein includes a prokaryotic SSB protein or a gp32 protein. In some embodiments of all aspects, at least one of the one or more nucleic acids (e.g., oligonucleotides) includes a detectable label.

In some embodiments of all aspects, the particles include one or more (e.g., two or more, or all) of a recombinase, a single stranded binding protein, and at least one of the one or more nucleic acids (in any combination). In some embodiments of all aspects, the reaction mixture includes a recombinase, a single-stranded binding protein, a polymerase, dNTPs, ATP, a primer, and a template nucleic acid.

In some embodiments of all aspects, the mixture includes one or more (e.g., two or more, three or more, four or more, five or more, six or more, seven or more, eight or more, or all) of a recombinase, a DNA polymerase, a single-stranded binding protein, a recombinase loading protein, ATP, dNTPs or a mixture of dNTPs and ddNTPs, a reducing agent, creatine kinase, a nuclease (e.g., an exonuclease III or endonuclease IV), a reverse transcriptase, a nucleic acid probe, a nucleic acid primer, and a template nucleic acid (in any combination).

In some embodiments of all aspects, the particles include a polymerase, dNTPs, ATP, a primer, and a template nucleic acid. In some embodiments of all aspects, the particles include a recombinase, a polymerase, dNTPs, ATP, a primer, and a template nucleic acid. In some embodiments of all aspects, the particles include a recombinase, a single-stranded binding protein, a polymerase, dNTPs, ATP, a primer, and a template nucleic acid. In some embodiments of all aspects, the particles include a polymerase, dNTPs, and ATP, and one or more (e.g., two, three, four, five, or six) additional agents selected from the group of a probe, a primer, a single-stranded binding protein, ddNTPs, a reducing agent, creatine kinase, a nuclease, and a reverse transcriptase. In some embodiments of all aspects, the particles include a recombinase, a polymerase, a reverse transcriptase, dNTPs, ATP, a primer, and a template nucleic acid.

In some embodiments of all aspects, the particles are about 0.5-20 μm in size, e.g., between about any two sizes selected from 0.5, 1, 1.5, 2, 2.5, 3, 4, 5, 6, 7, 8, 9, 10, 12, 15, 18, and 20 μm (e.g., about 1-10 μm in size).

In some embodiments of all aspects, approximately 10 to 5000 particles/nL, e.g., between any two numbers of particles selected from 10, 20, 50, 100, 200, 500, 1000, 2000, and 5000 particles per nL, are detected.

In some embodiments of all aspects, detecting particles in the mixture includes the use of one or more of microscopy, a microfluidic device, flow cytometry, and a camera. In some embodiments of all aspects, the particles are detected using charge-coupled detection (CCD).

In another aspect, the disclosure features a process that includes: (a) providing a recombinase polymerase amplification reaction mixture; (b) maintaining the reaction mixture under conditions that allow for the production of nucleic acid amplification products in the reaction mixture; and (c) detecting particles associated with the nucleic acid amplification products in the reaction mixture. In some embodiments, the detecting is performed within 10 minutes (e.g., within 9, 8, 7, 6, 5, 4, 3, 2, 1.5, or 1 minute) from when the maintaining begins.

In some embodiments of all aspects, the reaction mixture includes a crowding agent, e.g., one or more of polyethylene glycol (e.g., PEG1450, PEG3000, PEG8000, PEG10000, PEG14000, PEG15000, PEG20000, PEG250000, PEG30000, PEG35000, PEG40000, PEG compound with molecular weight between 15,000 and 20,000 daltons, or combinations thereof), polyvinyl alcohol, dextran and ficoll. In some embodiments, the reaction mixture contains polyethylene glycol as a crowding agent (e.g., any of the PEG compounds described herein or known in the art). In some embodiments, the reaction mixture contains polyvinyl alcohol as a crowding agent. In some embodiments, the crowding agent is present in the reaction mixture at a concentration between 1 to 12% by weight or by volume of the reaction mixture, e.g., between any two concentration values selected from 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, and 12.0%. In some embodiments, the crowding agent is present in the reaction mixture at a concentration that is sufficient to increase the amount of amplification in the reaction mixture.

In some embodiments of all aspects, the particles include one or more (e.g., two or more or all) of the recombinase, the single stranded binding protein, and at least one of the one or more nucleic acids (in any combination).

In some embodiments of all aspects, the reaction mixture includes one or more (e.g., two or more, three or more, four or more, five or more, six or more, seven or more, eight or more, or all) of a DNA polymerase, a recombinase loading protein, ATP, dNTPs or a mixture of dNTPs and ddNTPs, a reducing agent, creatine kinase, a nuclease (e.g., an exonuclease III or endonuclease IV), a single-stranded binding protein, a nucleic acid primer, a nucleic acid probe, reverse transcriptase, and a template nucleic acid (in any combination).

In some embodiments of all aspects, the reaction mixture contains a recombinase, a single-stranded binding protein, and one or more oligonucleotides. In some embodiments of all aspects, the reaction mixture includes a recombinase, a single-stranded binding protein, a polymerase, dNTPs, ATP, a primer, and a template nucleic acid.

In some embodiments of all aspects, the reaction mixture includes a polymerase, dNTPs, ATP, a primer, and a template nucleic acid. In some embodiments of all aspects, the reaction mixture includes a recombinase, a polymerase, dNTPs, ATP, a primer, and a template nucleic acid. In some embodiments of all aspects, the reaction mixture includes a recombinase, a single-stranded binding protein, a polymerase, dNTPs, ATP, a primer, and a template nucleic acid. In some embodiments of all aspects, the reaction mixture includes a polymerase, dNTPs, and ATP, and one or more (e.g., two, three, four, five, or six) additional agents selected from the group of a probe, a primer, a single-stranded binding protein, ddNTPs, a reducing agent, creatine kinase, a nuclease, and a reverse transcriptase. In some embodiments of all aspects, the reaction mixture includes a recombinase, a polymerase, a reverse transcriptase, dNTPs, ATP, a primer, and a template nucleic acid. In some embodiments of all aspects, the particles are about 0.5-20 µm in size, e.g., between about any two sizes selected from 0.5, 1, 1.5, 2, 2.5, 3, 4, 5, 6, 7, 8, 9, 10, 12, 15, 18, and 20 µm (e.g., about 1-10 µm in size).

In some embodiments of all aspects, approximately 10 to 5000 particles/nL, e.g., between any two numbers of particles selected from 10, 20, 50, 100, 200, 500, 1000, 2000, and 5000 particles per nL, are detected.

In some embodiments of all aspects, the detecting includes determining a number or proportion of particles associated with nucleic acid amplification products in the reaction mixture and, optionally, determining or estimating the concentration of template nucleic acid in the original mixture thereby. In some embodiments, the detecting includes detecting single particles associated with two or more distinct nucleic acid amplification products.

In another aspect, the disclosure features compositions that include (a) a first population of particles that includes a first recombinase, a first single-stranded DNA binding protein, and a first oligonucleotide; and (b) a second population of particles that includes a second recombinase, a second single-stranded DNA binding protein, and a second oligonucleotide, wherein the first and second oligonucleotides are different. In some embodiments, at least one of the first and second oligonucleotides includes a detectable label. In some embodiments, the first and second oligonucleotides include the same or different detectable labels. The first and second single-stranded DNA binding protein can be the same or different from each other. The first and second recombinase can be the same or different from each other.

In some embodiments of all aspects, the particles are about 0.5-20 µm in size, e.g., between about any two sizes selected from 0.5, 1, 1.5, 2, 2.5, 3, 4, 5, 6, 7, 8, 9, 10, 12, 15, 18, and 20 µm (e.g., about 1-10 µm in size).

In some embodiments of all aspects, approximately 10 to 5000 particles/nL, e.g., between any two numbers of particles selected from 10, 20, 50, 100, 200, 500, 1000, 2000, and 5000 particles per nL, are present in the compositions.

In some embodiments of all aspects, the compositions include a crowding agent, e.g., one or more of polyethylene glycol (e.g., PEG1450, PEG3000, PEG8000, PEG10000, PEG14000, PEG15000, PEG20000, PEG250000, PEG30000, PEG35000, PEG40000, PEG compound with molecular weight between 15,000 and 20,000 daltons, or combinations thereof), polyvinyl alcohol, dextran and ficoll. In some embodiments, the crowding agent is present in the composition at a concentration between 1 to 12% by weight or by volume of the reaction mixture, e.g., between any two concentration values selected from 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, and 12.0%.

In some embodiments of all aspects, the compositions further include one or more (e.g., two or more, three or more, four or more, five or more, six or more, seven or more, eight or more, or all) of a DNA polymerase, a recombinase loading protein, ATP, dNTPs or a mixture of dNTPs and ddNTPs, a reducing agent, creatine kinase, a nuclease (e.g., an exonuclease III or endonuclease IV), a nucleic acid probe, and a template nucleic acid (in any combination).

In some aspects, the disclosure features compositions that include one or more oligonucleotides describe herein and variants thereof. In some embodiments, the oligonucleotides can be used as primers and/or detection probes in methods of nucleic acid amplifications (e.g., isothermal nucleic acid amplifications such as RPA). The oligonucleotides described herein can include one or more detectable labels. Where an oligonucleotide is disclosed as including one or more detectable labels, alternative labels may be used at the same positions or at different positions within the oligonucleotide (e.g., at a position within 1, 2, 3, 4, 5, 6, 7, 8, 9, 10, 11, 12, 13, 14, 15, 16, 17, 18, 19, 20, 25, or 30 bases 5' or 3' of the disclosed position). In some embodiments, the oligonucleotides can include one or more abasic site mimics. Where an oligonucleotide includes one or more abasic site mimics, alternative abasic site mimics may be included at the same position or at different positions within the oligonucleotide (e.g., at a position within 1, 2, 3, 4, 5, 6, 7, 8, 9, 10, 11, 12, 13, 14, 15, 16, 17, 18, 19, 20, 25, or 30 bases 5' or 3' of the disclosed position). In some embodiments, a variant of an oligonucleotide described herein has twelve or fewer (e.g., eleven or fewer, ten or fewer, nine or fewer, eight or fewer, seven or fewer, six or fewer, five or fewer, four or fewer, three or fewer, two or fewer, or one or fewer) insertions, deletions, substitutions, and/or additions compared to the disclosed oligonucleotide sequence. In some embodiments, a variant of an oligonucleotide described herein has a sequence at least 80% (e.g., 85%, 90%, or 95%) identical to the disclosed oligonucleotide sequence.

In some embodiments, the particles are detected using fluorescence from the particles.

In certain embodiments, the particles are detected without using fluorescence from the particles.

In some embodiments, the particles are detected using fluorescence from the particles, phase contrast microscopy, luminescent detection, spectral (color) detection, magnetic detection, radioisotopic detection, and/or electrochemical detection. In some embodiments the particles can be detected using a combination of two of more (e.g., two, three, or four) of fluorescence from the particles, phase contrast microscopy, luminescent detection, spectral (color) detection, magnetic detection, radioisotopic detection, and electrochemical detection.

In some embodiments, some of the particles are detected using fluorescence from those particles, and other of the particles are detected without using fluorescence from these other particles. For example, the particles include a first subset of particles and a second subset of particles. The first subset of particles is detected using fluorescence from the first subset of particles, and the second subset of particles are detected without using fluorescence from the second subset of particles (e.g., phase contrast microscopy, luminescent detection, spectral (color) detection, magnetic detection, radioisotopic detection, and/or electrochemical detection).

In another aspect, the disclosure features a population of particles that includes a recombinase, a single-stranded DNA binding protein, and an oligonucleotide, wherein some of the particles are detected using fluorescence from those particles, and other of the particles are detected without using fluorescence from these other particles.

Also provided are kits including a recombinase, a single-stranded DNA binding protein, and an oligonucleotide for use in any of the methods described herein. Also provided are kits including any of the particles or compositions described herein and instructions for performing any of the methods described herein.

The processes and compositions disclosed herein can be used for the detection of nucleic acids, e.g., bacterial nucleic acids, mammalian nucleic acids, viral nucleic acids, fungal nucleic acids, or protozoan nucleic acids, and for the diagnosis of disorders or diseases associated with such nucleic acids.

As used herein the "size" of a particle refers to the largest cross-sectional dimension of the particle.

As used herein, an "oligonucleotide" refers to a nucleic acid polymer containing at least 10 (e.g., at least 12, 15, 20, 25, 30, 35, 40, 50, 60, 70, 80, 90, or 100) base units. In some embodiments, the oligonucleotide contains a total of less than 1 kb, 900 base units, 800 base units, 700 base units, 600 base units, 500 base units, 400 base units, 300 base units, 200 base units, or 100 base units. In some embodiments, an oligonucleotide can have 90 or fewer, 80 or fewer, 70 or fewer, 60 or fewer, 50 or fewer, 40 or fewer, 30 or fewer, or 20 or fewer base units. In some embodiments, an oligonucleotide has at least 10, 12, 14, 16, 18, or 20 base units.

As used herein, "cytometry" refers to methods and compositions for detecting, visualizing, and analyzing the properties of particles. The term as used herein does not denote the presence of cells. However, methods and compositions used for detecting, visualizing, and analyzing the properties of cells can be applied to the particles described herein.

As used herein, an "abasic site mimic" refers to a subunit position within a nucleic acid polymer in which a sugar or modified sugar moiety (e.g., glucose or deoxyglucose) is present, and the 1' carbon of the sugar or modified sugar moiety is not covalently bonded to a cyclic base structure (e.g., adenine, guanine, cytosine, thymine, uracil, or modified versions thereof). In some embodiments, the 1' carbon of the sugar or modified sugar moiety is covalently bonded to a hydrogen (e.g., tetrahydrofuran). In some embodiments, the 1' carbon of the sugar or modified sugar moiety is covalently bonded to another carbon that is not present in a cyclic base structure. In some embodiments, the 1' carbon of the sugar or modified sugar moiety is covalently bonded to a non-cyclic linker structure. In some embodiments, an abasic site mimic is recognized by an enzyme which processes and modifies abasic site mimics due to structural similarity to an abasic site (i.e. lack of a bulky base group attached to the sugar).

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims

BRIEF DESCRIPTION OF DRAWINGS

The patent or application file contains at least one drawing executed in color (FIGS. 1-13). Copies of this patent or patent application publication with color drawings will be provided by the Office upon request and payment of the necessary fee.

FIG. 16 shows line graphs (A-B) depicting amplification reactions in mixtures including T6 H66S UvsX and UvsY (std UvsX+UvsY), T6 H66S UvsX without UvsY (std UvsX−UvsY), T6 UvsX and UvsY (T6 UvsX+UvsY), and T6 UvsX without UvsY (T6 UvsX−UvsY).

DETAILED DESCRIPTION

Figure 1:
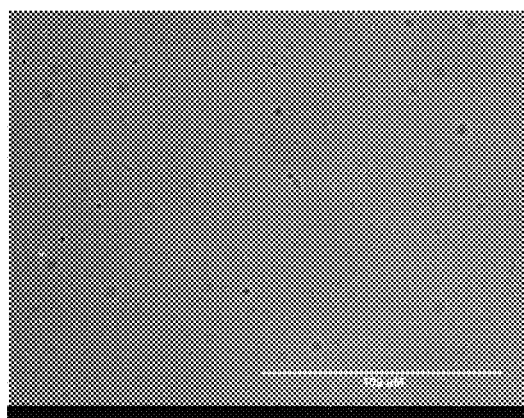
FIG. 1 shows micrographs depicting a single field of a mixture including particles. The scale bar indicates 100 μm. (A), differential interference contrast (DIC). (B), fluorescence. (C), merge.
Figure 1:
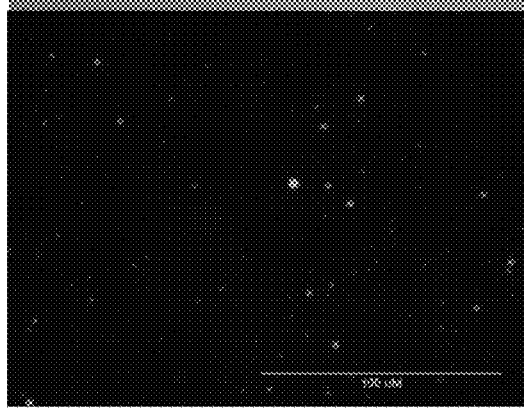
Figure 1:
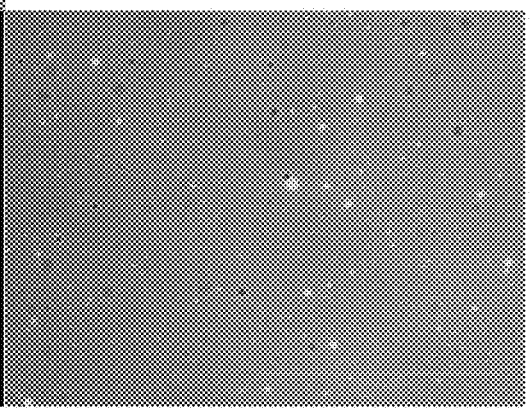

On microscopic observation, structures with the appearance of particles were observed within RPA mixtures. During the progress of the RPA nucleic acid amplification reaction, the particles are associated with loci of active amplification.

The particles observed were typically in the range of 1-10 µm in size, and were present at approximately 100-500 particles/nL. The particles were found to contain oligonucleotides present in the mixtures. Formation of the particles did not require the presence of magnesium. However, particles formed in the absence of a recombinase or a single-stranded DNA binding protein had an altered morphology. Formation of the particles in the absence of other agents, such as recombinase loading protein, DNA polymerase, creatine kinase, or exonucleases, did not significantly affect particle morphology. Additionally, particle formation was more efficient in the presence of crowding agents.

The particles were observed to be relatively stable in solution. Separate populations of particles could be mixed and remain distinct for a period of time following mixing.

Recombinase Polymerase Amplification

RPA is a method for amplification (e.g., isothermal amplification) of nucleic acids. In general, in a first step of RPA a recombinase is contacted with a first and a second nucleic acid primer to form first and second nucleoprotein primers. In general, in a second step the first and second nucleoprotein primers are contacted to a double stranded template nucleic acid to form a first double stranded structure at a first portion of the first strand of the template nucleic acid, and a second double stranded structure at a second portion of the second strand of the template nucleic acid, such that the 3' ends of the first nucleic acid primer and the second nucleic acid primer are oriented towards each other on a given DNA molecule. In general, in a third step the 3' end of the first and the second nucleoprotein primers are extended by DNA polymerases to generate first and second double stranded nucleic acids, and first and second displaced strands of nucleic acid. Generally, the second and third steps can be repeated until a desired degree of amplification is reached.

As described herein, RPA employs enzymes, known as recombinases, that are capable of pairing oligonucleotide primers with homologous sequences in template double-stranded DNA. In this way, DNA synthesis is directed to defined points in a template double-stranded DNA. Using two or more sequence-specific (e.g., gene-specific) primers, an exponential amplification reaction is initiated if the template nucleic acid is present. The reaction progresses rapidly and results in specific amplification of a sequence present within the template double-stranded DNA from just a few copies of the template DNA to detectable levels of the amplified products within minutes. RPA methods are disclosed, e.g., in U.S. Pat. No. 7,270,981; U.S. Pat. No. 7,399,590; U.S. Pat. No. 7,666,598; U.S. Pat. No. 7,435,561; US 2009/0029421; and WO 2010/141940, all of which are incorporated herein by reference.

RPA reactions contain a blend of proteins and other factors that support both the activity of the recombination element of the system, as well as those which support DNA synthesis from the 3' ends of oligonucleotides paired to complementary substrates. In some embodiments, the RPA reaction contains a mixture of a recombinase, a single-stranded binding protein, a polymerase, dNTPs, ATP, a primer, and a template nucleic acid. In some embodiments, a RPA reaction can include one or more of the following (in any combination): at least one recombinase; at least one single-stranded DNA binding protein; at least one DNA polymerase; dNTPs or a mixture of dNTPs and ddNTPs; a crowding agent; a buffer; a reducing agent; ATP or ATP analog; at least one recombinase loading protein; a first primer and optionally a second primer; a probe; a reverse transcriptase; and a template nucleic acid molecule, e.g., a single-stranded (e.g., RNA) or double stranded nucleic acid. In some embodiments, the RPA reactions can contain, e.g., a reverse transcriptase. Additional non-limiting examples of RPA reaction mixtures are described herein.

In some embodiments, the RPA reactions can contain a UvsX protein, a gp32 protein, and a UvsY protein. Any of the processes, compositions or particles described herein can contain, in part, e.g., a UvsX protein, a gp32 protein, and a UvsY protein. For example, any of the processes, compositions, or particles described herein can contain, in part, T6H66S UvsX, Rb69 gp32, and Rb69 UvsY.

In some embodiments, the RPA reactions can contain a UvsX protein and a gp32 protein. For example, any of the processes, compositions, or particles described herein can contain, in part, e.g., a UvsX protein and a gp32 protein.

One protein component of an RPA reaction is a recombinase, which may originate from prokaryotic, viral or eukaryotic origin. Exemplary recombinases include RecA and UvsX (e.g., a RecA protein or UvsX protein obtained from any species), and fragments or mutants thereof, and combinations thereof. The RecA and UvsX proteins can be obtained from any species. RecA and UvsX fragments or mutant proteins can also be produced using the available RecA and UvsS protein and nucleic acids sequences, and molecular biology techniques (see, e.g., the mutant forms of UvsX described in U.S. Pat. No. 8,071,308). Exemplary UvsX proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Additional exemplary recombinase proteins include archaebacterial RADA and RADB proteins and eukaryotic (e.g., plant, mammal, and fungal) Rad51 proteins (e.g., RAD51, RAD51B, RAD51C, RAD51D, DMC1, XRCC2, XRCC3, and recA) (see, e.g., Lin et al., *Proc. Natl. Acad. Sci. U.S.A.* 103:10328-10333, 2006).

In any process of this disclosure, the recombinase (e.g., UvsX) may be a mutant or hybrid recombinase. In some embodiments, the mutant UvsX is an Rb69 UvsX that includes at least one mutation in the Rb69 UvsX amino acid sequence, wherein the mutation is selected from the group consisting of (a) an amino acid which is not histidine at position 64, a serine at position 64, the addition of one or more glutamic acid residues at the C-terminus, the addition of one or more aspartic acid residues at the C-terminus, and a combination thereof. In other embodiments, the mutant UvsX is a T6 UvsX having at least one mutation in the T6 UvsX amino acid sequence, wherein the mutation is selected from the group consisting of (a) an amino acid which is not histidine at position 66; (b) a serine at position 66; (c) the addition of one or more glutamic acid residues at the C-terminus; (d) the addition of one or more aspartic acid residues at the C-terminus; and (e) a combination thereof. Where a hybrid recombinase protein is used, the hybrid protein may, for example, be a UvsX protein that includes at least one region that includes an amino acid sequence derived from a different UvsX species. The region may be, for example, the DNA-binding loop-2 region of UvsX.

Additionally, one or more single-stranded DNA binding proteins can be used to stabilize nucleic acids during the various exchange reactions that are ongoing in the reaction. The one or more single-stranded DNA binding proteins can be derived or obtained from any species, e.g., from a prokaryotic, viral or eukaryotic species. Non-limiting exemplary single-stranded DNA binding proteins include *E. coli* SSB and those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Additional examples of single-stranded DNA binding proteins include *A. denitrificans* Alide_2047, *Burkholderia thailandensis* BthaB_33951, *Prevotella pallens* HMPREF9144_0124, and eukaryotic single-stranded DNA binding protein replication protein A.

The DNA polymerase may be a eukaryotic or prokaryotic polymerase. Examples of eukaryotic polymerases include pol-alpha, pol-beta, pol-delta, pol-epsilon, and mutants or fragments thereof, or combinations thereof. Examples of prokaryotic polymerase include *E. coli* DNA polymerase I (e.g., Klenow fragment), bacteriophage T4 gp43 DNA polymerase, *Bacillus stearothermophilus* polymerase I large fragment, Phi-29 DNA polymerase, T7 DNA polymerase, *Bacillus subtilis* Pol I, *Staphylococcus aureus* Pol I, *E. coli* DNA polymerase I, *E. coli* DNA polymerase II, *E. coli* DNA polymerase III, *E. coli* DNA polymerase IV, *E. coli* DNA polymerase V, and mutants or fragments thereof, or combinations thereof. In some embodiments, the DNA polymerase lacks 3'-5' exonuclease activity. In some embodiments, the DNA polymerase has strand-displacing properties, e.g., large fragments of prokaryotic polymerases of class I or pol V.

Any of the process of this disclosure may be performed in the presence of a crowding agent. In some embodiments, the crowding agent may include one or more of polyethylene glycol, polyethylene oxide, polyvinyl alcohol, polystyrene, Ficoll, dextran, poly(vinylpyrrolidone) (PVP), and albumin. In some embodiments, the crowding agent has a molecular weight of less than 200,000 daltons. Further, the crowding agent may be present, e.g., in an amount of about 0.5% to about 15% weight to volume (w/v).

If a recombinase loading protein is used, the recombinase loading protein may be of prokaryotic, viral or eukaryotic origin. Exemplary recombinase loading proteins include *E. coli* RecO, *E. coli* RecR, UvsY, and mutants or fragments thereof, or combinations thereof. Exemplary UvsY proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. In any of the processes of this disclosure, the recombinase loading agent may be derived from a myoviridae phage. The myoviridae phage may be, for example, T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2.

Further, any of the processes of this disclosure may be performed with a blocked primer. A blocked primer is a primer which does not allow elongation with a polymerase. Where a blocked primer is used, an unblocking agent can be used to unblock the primer to allow elongation. The unblocking agent may be an endonuclease or exonuclease which can cleave the blocking group from the primer. Exemplary unblocking agents include *E. coli* exonuclease III and *E. coli* endonuclease IV.

In some embodiments, the processes of this disclosure can include: contacting a recombinase with a first and a second nucleic acid primer and a third extension blocked primer which contains one or more noncomplementary or modified internal residue to form a first, second, and third nucleoprotein primer; contacting the first and second nucleoprotein primers to the double stranded target nucleic acid to form a first double stranded structure between the first nucleoprotein primer and the first strand of DNA at a first portion of the first strand (forming a D loop) and a second double stranded structure between the second nucleoprotein primer and the second strand of DNA at a second portion of the second strand (forming a D loop), such that the 3' ends of the first nucleoprotein primer and the second nucleoprotein primer are oriented toward each other on the same target nucleic acid molecule with a third portion of target nucleic acid present between the 5' ends of the first and second primer; and extending the 3' end of the first nucleoprotein primer and second nucleoprotein primer with one or more polymerases and dNTPs to generate a first amplified target nucleic acid; contacting the first amplified target nucleic acid to the third nucleoprotein primer to form a third double stranded structure in the first amplified target nucleic acid (forming a D loop) in the presence of a nuclease, wherein the nuclease specifically cleaves the noncomplementary internal residue only after the formation of the third double-stranded structure to form a third 5' primer and a third 3' extension blocked primer; and extending the 3' end of the third 5' primer with one or more polymerase and dNTP to generate a second double-stranded amplified nucleic acid.

In some embodiments, the processes include a first and second primer to amplify a first portion present within a double-stranded target nucleic acid to generate a first amplified product, and at least one additional primer that can be used to amplify a contiguous sequence present within the first amplified product (e.g., an additional third primer that can be used in combination with, e.g., the first or the second primer, to amplify a contiguous sequence present within the first amplified product). In some embodiments, the processes include a first and second primer to amplify a first portion present within a double-stranded target nucleic acid to generate a first amplified product, and a third and fourth primer that can be used to amplify a contiguous sequence present within the first amplified product.

In some embodiments, the processes can include, e.g., a forward primer and a reverse primer. In some embodiments, the processes can include at least one blocked primer which comprises one or more noncomplementary or modified internal residues (e.g., one or more noncomplementary or modified internal residues that can be recognized and cleaved by a nuclease, e.g., DNA glycosylase, AP endonuclease, fpg, Nth, MutY, MutS, MutM, *E. coli*. MUG, human MUG, human Ogg1, a vertebrate Nei-like (Neil) glycosylase, Nfo, exonuclease III, or uracil glycosylase). Additional non-limiting examples of nucleic acids (e.g., primers and probes) that can be included in a process are described herein.

In some embodiments, the processes can include a primer or probe that is nuclease resistant, e.g., a primer or probe that contains at least one (e.g., at least two, three, four, five, six, seven, or eight) phosphorothioate linkages.

Any of the processes of this disclosure may be performed in the presence of heparin. Heparin may serve as an agent to reduce the level of non-specific primer noise, and to increase the ability of *E. coli* exonuclease III or *E. coli* endonuclease IV to rapidly polish 3' blocking groups or terminal residues from recombination intermediates.

Based on the particular type of reaction, the mixture can also contain one or more of buffers, salts, and nucleotides. The reaction mixture can be maintained at a specific temperature or temperature range appropriate to the reaction. In some embodiments, the temperature is maintained at or below 80° C., e.g., at or below 70° C., at or below 60° C., at or below 50° C., at or below 40° C., at or below 37° C., at or below 30° C., or at or below room temperature. In some embodiments, the temperature is maintained at or above 4° C., at or above 10° C., at or above 15° C., at or above 20° C., at or above room temperature, at or above 25° C., at or above 30° C., at or above 37° C., at or above 40° C., at or above 50° C., at or above 60° C., or at or above 70° C. In some embodiments, the reaction mixture is maintained at room or ambient temperature. In some embodiments, the Celsius-scale temperature of the mixture is varied by less than 25% (e.g., less than 20%, less than 15%, less than 10%, or less than 5%) throughout the reaction time and/or the temperature of the mixture is varied by less than 15° C. (e.g., less than 10° C., less than 5° C., less than 2° C., or less than 1° C.) throughout the reaction time.

Detection of amplification, e.g., in real time, may be performed by any method known in the art. In some embodiments, one or more primers or probes (e.g., molecular beacon probes) are labeled with one or more detectable labels. Exemplary detectable labels include enzymes, enzyme substrates, coenzymes, enzyme inhibitors, fluorescent markers, quenchers, chromophores, magnetic particles or beads, redox sensitive moieties (e.g., electrochemically active moieties), luminescent markers, radioisotopes (including radionucleotides), and members of binding pairs. More specific examples include fluorescein, phycobiliprotein, tetraethyl rhodamine, and beta-galactosidase. Binding pairs may include biotin/avidin, biotin/strepavidin, antigen/antibody, ligand/receptor, and analogs and mutants of the binding pairs.

It should be noted that a fluorescence quencher is also considered a detectable label. For example, the fluorescence quencher may be contacted to a fluorescent dye and the amount of quenching is detected.

Particle Detection

Detection and monitoring of the particles can be performed using any suitable method. Exemplary methods include microscopy, light scattering, flow cytometry, and microfluidic methods.

In some embodiments, the particles can be detected using microscopy, e.g., differential interference contrast or fluorescence microscopy, to directly observe the particles at high magnification. With the aid of a computer, microscope images can be automatically obtained and analyzed. Additionally, microscopy can allow for continual or frequent monitoring of at least a portion of a mixture containing particles.

In some embodiments, the particles can be detected using flow cytometry. In flow cytometry, one or more beams of light, e.g., each of a single wavelength, are directed onto a hydrodynamically-focused stream of fluid. Suspended particles passing through the beams scatter the light, and fluorescent chemicals found in the particle or attached to the particle may be excited. The scattered and/or fluorescent light is picked up by detectors within the device, from which information about particle size and fluorescence can be determined. Modern flow cytometers can analyze several thousand particles every second, in "real time," and can actively separate and isolate particles having specified properties.

In some embodiments, the particles can be detected using cytometry methods, devices, and systems as disclosed in US 2009/0079963, US 2010/0179068, and WO 2009/112594.

In some embodiments, the particles can be detected using microfluidic methods, devices, and systems. For example, the particles can be detected using a lab-on-a-chip device or system, or the like. See, e.g., U.S. Patent Application Publication Nos. 2009/0326903 and 2009/0297733

In some embodiments, the particles can be detected using a device or system suitable for point-of-care, field, or consumer use. For example, a device (e.g., a lap-on-a-chip device) can include a recombinase, a polymerase, a single-stranded binding protein, ATP, dNTPs, and a primer or probe. In some embodiments, a device can be provided that contains a recombinase, a polymerase, a single-stranded binding protein, ATP, dNTPs, and a primer or probe, where one of the recombinase, the polymerase, the primer or probe, or recombinase is covalently attached or non-covalently bound (e.g., through use of an affinity tag) to a surface. In some embodiments, particles can be placed in multiple single wells in a multi-well plate.

In any of the disclosed methods, where desired the particles may be fixed prior to detection. For example, the particles can be fixed by treatment with an aldehyde (e.g., formaldehyde, paraformaldehyde, or glutaraldehyde) to cross-link proteins and nucleic acids in the sample, effectively stopping the progress of reactions in the mixture and allowing for observation of the particles in the state at which the reaction was stopped. By fixing the mixtures, the particles may be detected at a later point in time, potentially simplifying processing and detection.

Oligonucleotides

Oligonucleotides as disclosed herein may serve as amplification primers and/or detection probes. In some embodiments, the oligonucleotides are provided as a set of two or more (e.g., two, three, four, or more) oligonucleotides, e.g., for use in an amplification method (e.g., as described herein).

Oligonucleotides can be synthesized according to standard phosphoroamidate chemistry, or otherwise. Modified bases and/or linker backbone chemistries may be desirable and functional in some cases and can be incorporated during synthesis. Additionally oligonucleotides may be modified with groups that serve various purposes e.g. fluorescent groups, quenchers, protecting (blocking) groups (reversible or not), magnetic tags, proteins etc.

In some embodiments, the oligonucleotide used herein can contain a contiguous sequence (e.g., at least 10 base units) that is at least 90% identical (e.g., at least 91%, 92%, 93%, 94%, 95%, 96%, 97%, 98%, 99%, or 100%) to a contiguous sequence present within a target nucleic acid. The percent identity or homology between two sequences can be determined using a mathematical algorithm. A non-limiting example of a mathematical algorithm utilized for the comparison of two sequences is the algorithm of Karlin and Altschul (1990) Proc. Natl. Acad. Sci. USA, 87:2264-68, modified as in Karlin and Altschul (1993) Proc. Natl. Acad. Sci. USA, 90:5873-77. Such an algorithm is incorporated into the NBLAST program of Altschul, et al., (1990); J. Mol. Biol. 215:403-410. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the NBLAST program can be used. See online at ncbi.nlm.nih.gov.

The oligonucleotides may include one or more detectable labels. The detectable label may be a fluorophore, an enzyme, a quencher, an enzyme inhibitor, a radioactive label, a redox sensitive moiety (e.g., an electrochemically active moiety) one member of a binding pair and a combination thereof. In some embodiments, the oligonucleotides can include both a fluorophore and a quencher. The quencher may be close to the fluorophore to suppress the fluorescence of the fluorophore. For example, the separation between the fluorophore and the quencher may be 0 to 2 bases, 0 to 5 bases, 0 to 8 bases, 0 to 10 bases, 3 to 5 bases, 6 to 8 bases, and 8 to 10 bases. The fluorophore and quencher may be any fluorophore and quencher known to work together including, but not limited to, the fluorophore and quenchers any of the fluorophores described in this disclosure. Where the detectable label is a fluorophore or a quencher, it may be attached to the oligonucleotide by a fluorophore-dT amidite residue or quencher-dT amidite residue respectively. Other attachments are possible and widely known.

In another aspect, either the fluorophore or the quencher may be attached to a modified internal residue and the fluorophore and quencher can be separated following cleavage of the modified internal residue by the nuclease.

While any fluorophore may function for the methods of the invention, fluorescein, FAM, TAMRA, and Texas Red are exemplary fluorophores. Exemplary quenchers include a dark quencher which may be, for example, Dark Quencher 1, Dark Quencher 2, Black Hole Quencher 1 or Black Hole Quencher 2.

In some embodiments, the oligonucleotides can include a modified internal residue. The modified internal residue may be any chemical structure (residue) that cannot form a Watson-Crick base pairing structure with its corresponding base in a double stranded nucleic acid structure. The term "modified internal residue," also includes, at least, any residue not normally found in DNA—that is any residue which is not an "A", "G", "C" or "T" such as, for example uracil or inosine. In some embodiments, the modified internal residue is inosine, uracil, 8-oxoguanine, thymine glycol, or an abasic site mimic. Preferred abasic site mimics include a tetrahydrofuran residue or D-spacer (which can be produced as a product of employing a 5'-O-Dimethoxytrityl-1', 2'-Dideoxyribose-3'-[(2-cyanoethyl)-(N,N-diisopropyl)]-phosphoramidite during oligonucleotide synthesis.

In some embodiments, the oligonucleotides are extension blocked. An extension blocked oligonucleotide is blocked at its 3' end so that it cannot normally be elongated by polymerase and dNTP even in the presence of a complimentary template. Methods of blocking an oligonucleotide are well known and include, at least, the inclusion of a blocked 3' nucleotide. The blocked 3' nucleotide may contain, for example, a blocking group that prevents polymerase extension. Generally, the blocking groups are attached to the 3' or 2' site of the 3' sugar residue but other locations of attachments are possible. One of the most common 3' blocking methods is to place a dideoxy sugar at the 3' end of an oligonucleotide. The blocking group may be, for example, a detectable label.

In some embodiments, the oligonucleotides disclosed herein may be modified by incorporation of one or more detectable labels, modified residues (e.g., modified internal residues), and blocking groups. When the oligonucleotide disclosed herein includes one or more detectable labels, modified residues (e.g., modified internal residues), and blocking groups, the oligonucleotide without such modifications or with additional modifications is also included in the disclosure. Additionally, an oligonucleotide as disclosed herein that includes one or more detectable labels, modified residues (e.g., modified internal residues), and blocking groups may have such a moiety replaced by another detectable label, modified residue (e.g., modified internal residue), or blocking group, e.g., a detectable label, modified residue (e.g., modified internal residue), or blocking group as disclosed herein.

Applications

The methods and compositions disclosed herein can be used, for example, to detect the number of copies of a target nucleic acid and to monitor amplification of a sequence present within a target nucleic acid. In some embodiments of the present methods, the target nucleic acids can be detected at low copy numbers and in relatively crude samples. In some embodiments, the detected nucleic acid is a bacterial nucleic acid, e.g., from a bacterium selected from *Chlamydia trachomatis, Neisseria gonorrhea*, Group A *Strepto-* coccus, Group B *Streptococcus*, *Clostridium difficile*, *Escherichia coli*, *Mycobacterium tuberculosis*, *Helicobacter pylori*, *Gardnerella vaginalis*, *Mycoplasma hominis*, *Mobiluncus* spp., *Prevotella* spp., and *Porphyromonas* spp, or from another bacterium described herein or known in the art. In some embodiments, the detected nucleic acid is a mammalian nucleic acid, e.g., a nucleic acid is associated with tumor cells. In some embodiments, the detected nucleic acid is a viral nucleic acid, e.g., from HIV, influenza virus, or dengue virus, or from another virus. In some embodiments, the detected nucleic acid is a fungal nucleic acid, e.g., from *Candida albicans* or another fungus. In some embodiments, the detected nucleic acid is a protozoan nucleic acid, e.g., from *Trichomonas* or another protozoan. The methods and compositions disclosed herein can be used in the diagnosis of a disorder or state associated with a detected nucleic acid, e.g., a bacterial nucleic acid, mammalian nucleic acid, viral nucleic acid, fungal nucleic acid, or protozoan nucleic acid (e.g., as disclosed herein). For example, the methods and compositions provided herein can be used to diagnose a bacterial infection, a viral infection, a fungal infection, or a parasitic infection. In some embodiments, the detected nucleic acid is a nucleic acid from: influenza A or a variant thereof, influenza B or a variant thereof, methicillin-resistant *Staphylococcus aureus* (MRSA), *C. difficile*, *M tuberculosis*, *Chlamydia* species (e.g., *Chlamydia trachomatis*), *N. gonorrhoeae*, *Treponema pallidum*, human papilloma virus (HPV) (e.g., HPV variants type 16 and type 18), hepatitis virus (e.g., hepatitis A, B, and C), or a circulating cancer cell. In some embodiments, the methods and compositions provided herein can be used to diagnose MRSA infection, *C. difficile* infection, tuberculosis, chlamydia infection, gonorrhea, syphilis, HPV infection, hepatitis viral infection, or HPV infection. The methods and compositions disclosed herein can be used in quantification of nucleic acids. "Digitalization" of nucleic acid amplification/detection reactions is a recent approach to allow for accurate counting of template molecules (see, e.g., Vogelstein, 1999, Proc. Natl. Acad. Sci. USA, 96:9236). Typically in these methods, spatial separation of the reaction mixture into the required micro-compartments (typically in the nanoliter range) is achieved by physically splitting an amplification reaction, e.g. by pressing it under pressure into suitable microfluidic cassettes or by dispersing it in a suitable emulsion. Without wishing to be bound by theory, if the particles disclosed herein are active centers of amplification, then the presence of the particles constitutes an inherent compartmentalization of the reaction mixture that may be used in quantification. For example, by counting the number of "active" RPA particles (e.g., those associated with the generation of a fluorescent signal) one can measure or estimate the number of template nucleic acid molecules present in the reaction mixture.

The methods can also be used to detect the physical linkage of two or more nucleic acids. In many molecular biology applications the detection of physical linkage of two different genetic markers present in a given sample is important. For example, the mere presence of a bacterial species marker and an antibiotic-resistance marker in a given sample does not deliver information about whether both markers are present in the same bacteria (e.g., on the same nucleic acid), or whether the markers are present in separate co-colonizing bacteria species. Demonstrating that the two markers are linked on a single piece of genomic DNA associates the antibiotic resistance with a particular pathogen. The co-localization of the two markers can deliver vital diagnostic information in this scenario.

The methods and compositions described herein can be used to demonstrate that the sites or locations of two amplification events for two nucleic acids are overlapping, providing information about the physical linkage of the nucleic acids. In contrast, separable amplification events can indicate the presence of both nucleic acids, but on separate segments of DNA (e.g., in two co-colonizing species of bacteria). In some embodiments, the linkage of two nucleic acid sequences can be detected by observing active amplification products of both localized to a single particle in a reaction mixture. In other embodiments, the linkage of two nucleic acid sequences on a single segment of DNA can be detected by observing "tethering" of two particles, each amplifying one of the nucleic acids, by the DNA segment.

In some embodiments, observation of the particles disclosed herein can be used in methods of quality control. For example, a relationship between particle appearance (number, size, density) and RPA performance can be used to generate an analytical parameter to predict RPA reaction quality prior to amplification. This could be used for general quality control purposes (e.g., to check what type/number of particles are present in a given reaction mixture), or to monitor the effect of changes in production procedures (e.g., stabilization processes) or in storage conditions, etc.

In some embodiments, the methods and compositions disclosed herein can be used to obtain results of amplification reactions within minutes (e.g., within 8, 7, 6, 5, 4, 3, 2, 1.5, or 1 minute) from the start of the reaction. Typically, monitoring amplification reactions by detecting the accumulation of fluorescence signal is performed "in bulk", i.e. the signals generated by individual template molecules is integrated over the entire given reaction volume, producing a detectable fluorescence response in 5-8 minutes. In contrast, observing the fluorescence signal generated at RPA particles may also in principle be used to shorten the time to result in a reaction. This result is due, at least in part, to higher sensitivity of detection under high magnification in defined loci (e.g., particles).

The fluorescence signal strength of standard RPA reactions, typically performed and monitored 'in bulk', does profit from mixing steps performed during the incubation, especially if very low amounts of starting template material are used. Observing amplification reactions directly at particles can reduce any variation introduced by mixing.

EXAMPLES

Example 1

Particles in Recombinase Polymerase Amplification Mixtures

This example describes the observation of particles containing oligonucleotides within RPA mixtures. Freeze dried mixtures of RPA reaction components including FAM labeled oligonucleotides were obtained by preparing a mixture containing 2.96 µg Creatine Kinase, 13.1 µg Rb69 gp32, 18.1 µg T6 H66S UvsX, 5.15 µg Rb69 UvsY, 5.38 µg Exonuclease III and 5.0 µg DNA Polymerase (large fragment of *S. aureus* polymerase I) in 80 µl 9.38 mM Tris Acetate, pH 8.3, 3.13 mM DTT, 2.5% PEG, 3.75% trehalose, 31.3 mM phosphocreatine, 1.56 mM ATP, 750 µM dNTPmix (188 µM each of dATP, dTTP, dCTP and dGTP), 388 nM Spy1258F2 (CACAGACACTCGACAAG TCCT-CAATCAAACCTTG; SEQ ID NO:1), 363 nM Spy1258R2 (CAGAAATCCT TGATGAGTTGCGGAAATTTGAGGT; SEQ ID NO:2) and 75 nM Spy1258exoP1 (CCTTGTC- CTACCTTATAGAACATAGAGAATQTHFAACCG-CACTCGCTAC; F=FAM-dT, H=THF (abasic site mimic), Q=BHQ-1-dT, 3'=block c3spacer; SEQ ID NO:3) and freeze-drying the mixture in 0.2-mL tubes. The dried reagents were resuspended in 46.5 µL rehydration buffer (48 mM Tris acetate, 133.8 mM KOAc, 2% PEG)+3.5 µL water and vortexed. These mixtures did not contain nucleic acid template or magnesium. Ten microliters of the mixture was transferred to a microscope slide and imaged using differential interference contrast (DIC) and fluorescence microscopy at 40× magnification (FIG. 1 (A-C)). Particles of about 1-10 microns in size were observed using DIC (FIG. 1 (A)) or fluorescence (FIG. 1 (B)), and when the two images were merged (FIG. 1 (C)). Approximately 100-500 particles/nL were observed (field of view at 40× magnification was equivalent to 1.55 nL of the mixture).

Figure 2:
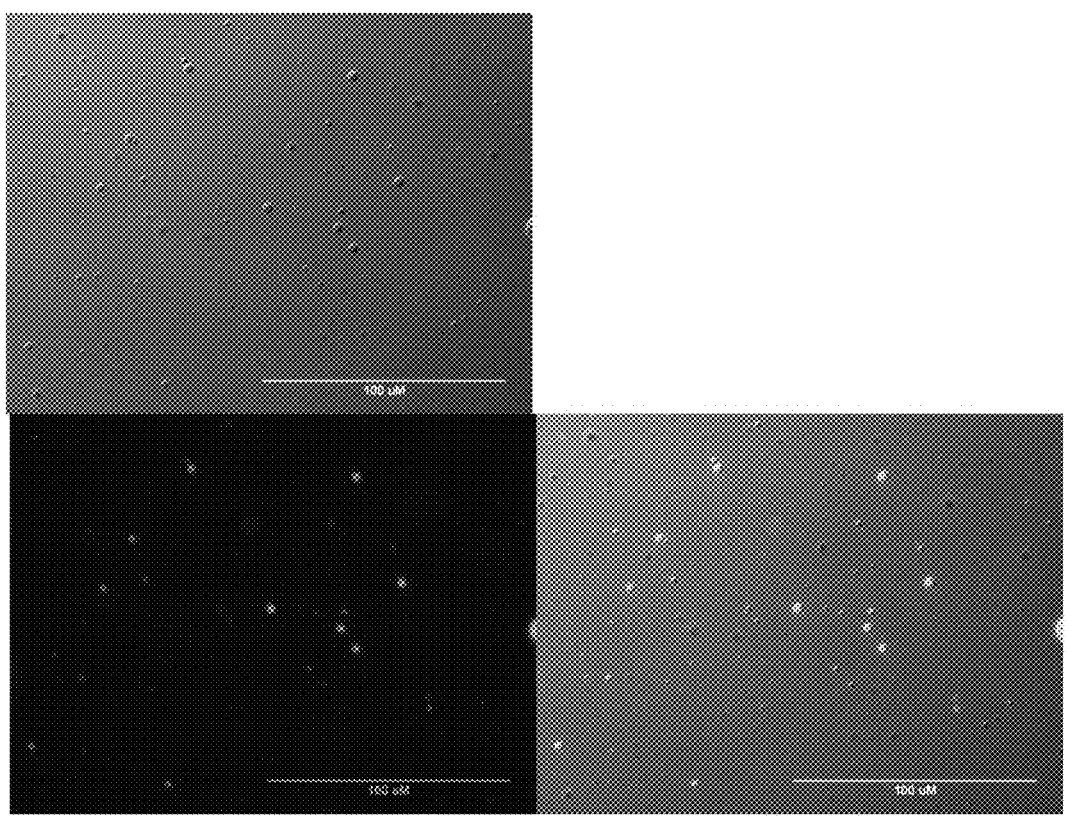
FIG. 2 shows micrographs depicting a single field of a mixture including particles and a template nucleic acid. The scale bar indicates 100 μm. (A), DIC. (B), fluorescence. (C), merge.

In a separate experiment, mixtures were prepared as above but substituting 2.5 µL water and 1 µL of a *Streptococcus pyogenes* genomic DNA preparation (100 copies/µl) for the 3.5 µL water. The mixture was vortexed and imaged as above (FIG. 2 (A-C)). Similar particles as above were observed using DIC (FIG. 2 (A)) or fluorescence (FIG. 2 (B)), and when the two images were merged (FIG. 2 (C)).

This example demonstrates that particles are formed in RPA mixtures, and that the particles are not dependent upon the inclusion of template or magnesium.

Example 2

Crowding Agents Stimulate Particle Formation

Figure 3:
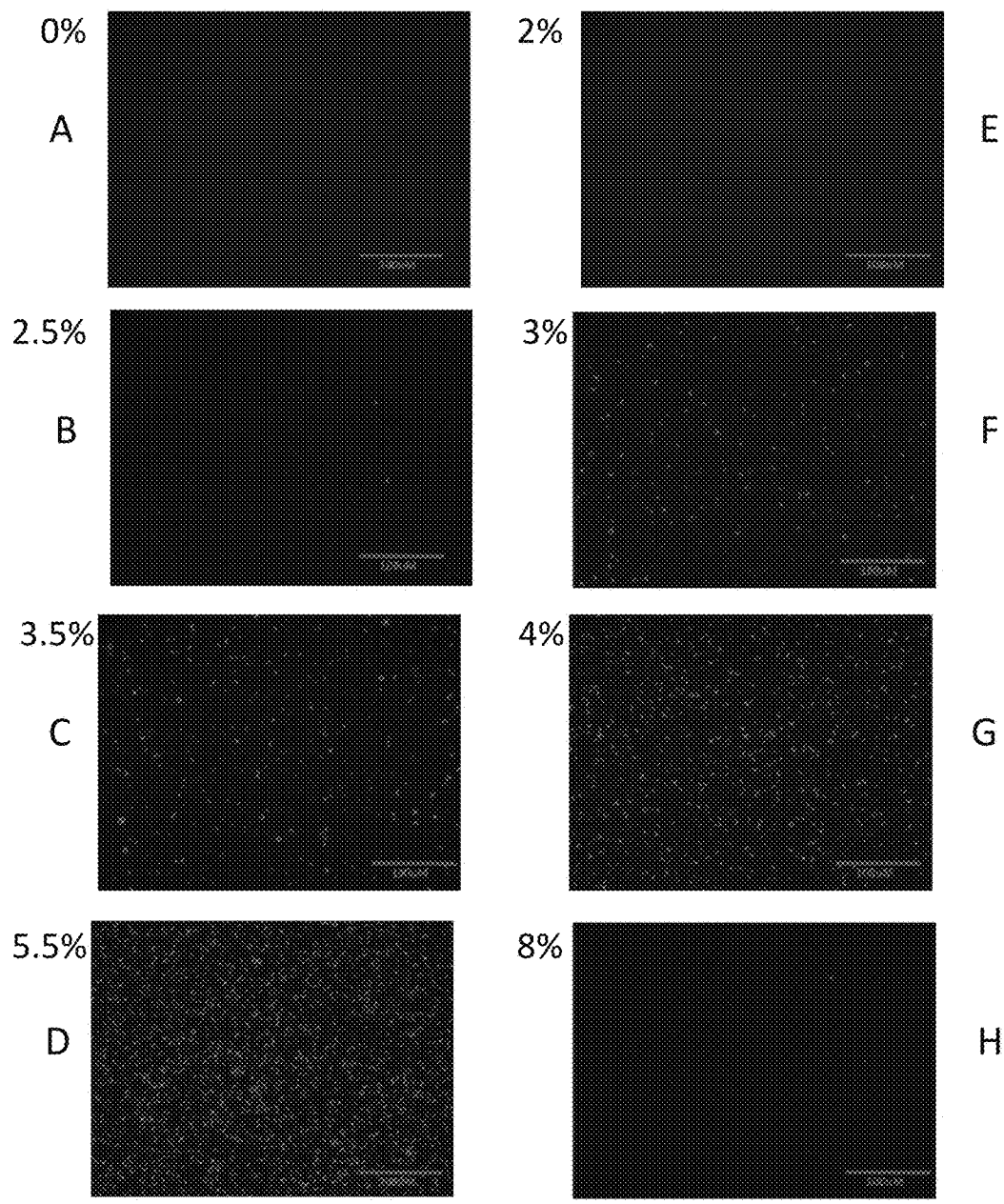
FIG. 3 shows fluorescence micrographs (A-H) depicting mixtures including the indicated concentrations of polyethylene glycol (PEG).

To determine the effects of crowding agents on particle formation, fresh RPA mixtures were prepared containing 2.96 µg Creatine Kinase, 13.1 µg Rb69 gp32, 18.8 µg T6 H66S UvsX, 2.5 µg Rb69 UvsY, 5.38 µg Exonuclease III and 5.0 µg DNA Polymerase in 50 mM Tris Acetate, pH 8.3, 100 mM KOAc, 5 mM DTT, 1.2 mM dNTP mix (300 µM each of dATP, dTTP, dCTP and dGTP), 50 mM phosphocreatine, 2.5 mM ATP, 6% trehalose, 14 mM MgAc, 30 nM HIV p2LFtexas (Texas red-labeled oligo AGAATTACAA-AAACAAATTACAAAAATTCA5AATTTTCGGGTTT; 3' dA blocked, 5' Texas Red, 5=dSpacer; SEQ ID NO:4), 420 nM Spy1258F2 (CACAGACACTCGACAAGTCCTCAAT-CAAACCTTG; SEQ ID NO:5), and 390 nM Spy1258R2 (CAGAAATCCTTGATGAGTTGCGGAAATTTGAGGT; SEQ ID NO:6). PEG was included in each mixture at 0%, 2%, 2.5%, 3%, 3.5%, 4%, 5.5%, or 8%. The mixtures were mixed by pipette and 10 µL of each was transferred to a microscope slide. Imaging was performed using differential interference contrast (DIC) and fluorescence microscopy at 40× magnification. The number of particles observed increased with increasing PEG concentration up to 5.5% (FIG. 3 (A-G)). Fewer particles were observed at 8% PEG (FIG. 3 (H)).

This example demonstrates that PEG can enhance formation of particles in RPA mixtures.

Example 3

Contribution of Mixture Components to Particle Formation

To determine the contribution of the RPA mixture components to particle formation, mixtures were prepared as in Example 2 with 5.5% PEG, except that individual components were excluded in each reaction. The mixtures were imaged as above using DIC and fluorescence microscopy.

Figure 4:
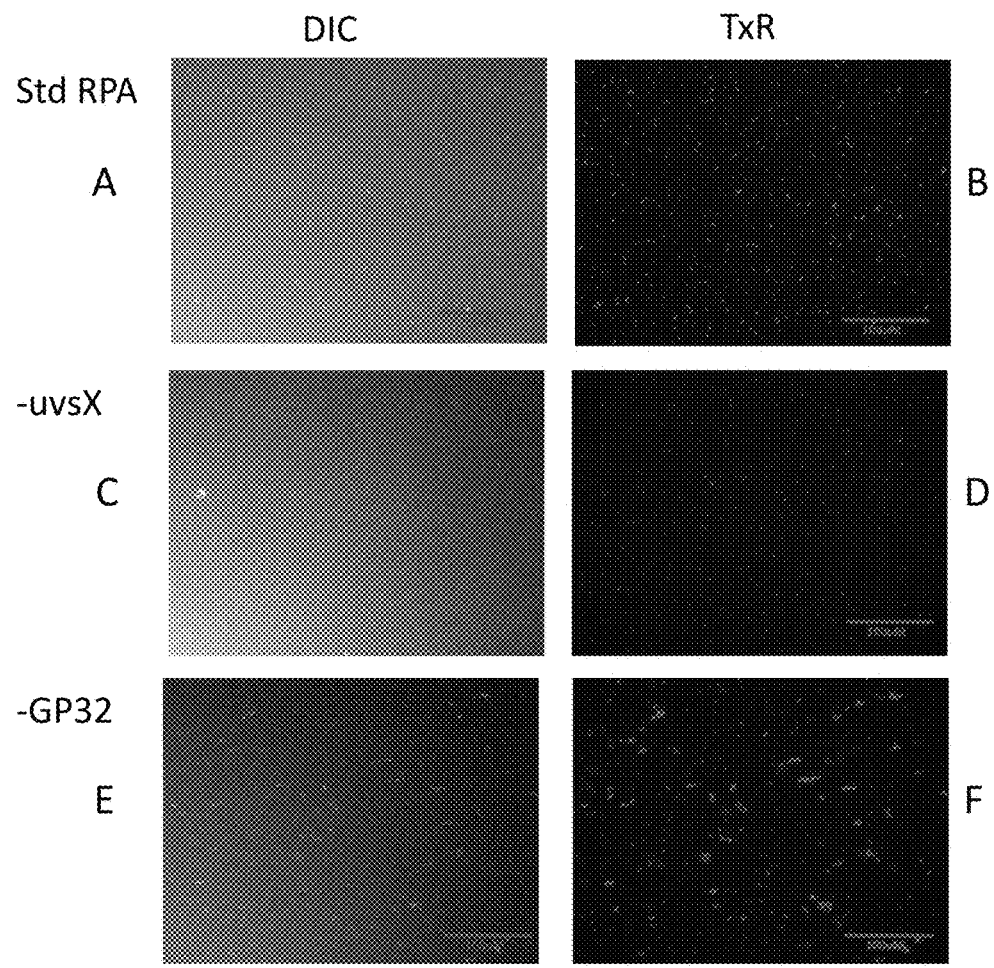
FIG. 4 shows micrographs depicting mixtures including particles. (A) and (B) are a standard mixture. (C) and (D) are the standard mixture excluding UvsX. (E) and (F) are the standard mixture excluding gp32. (A), (C), (E), DIC. (B), (D), (F), fluorescence.
Figure 5:
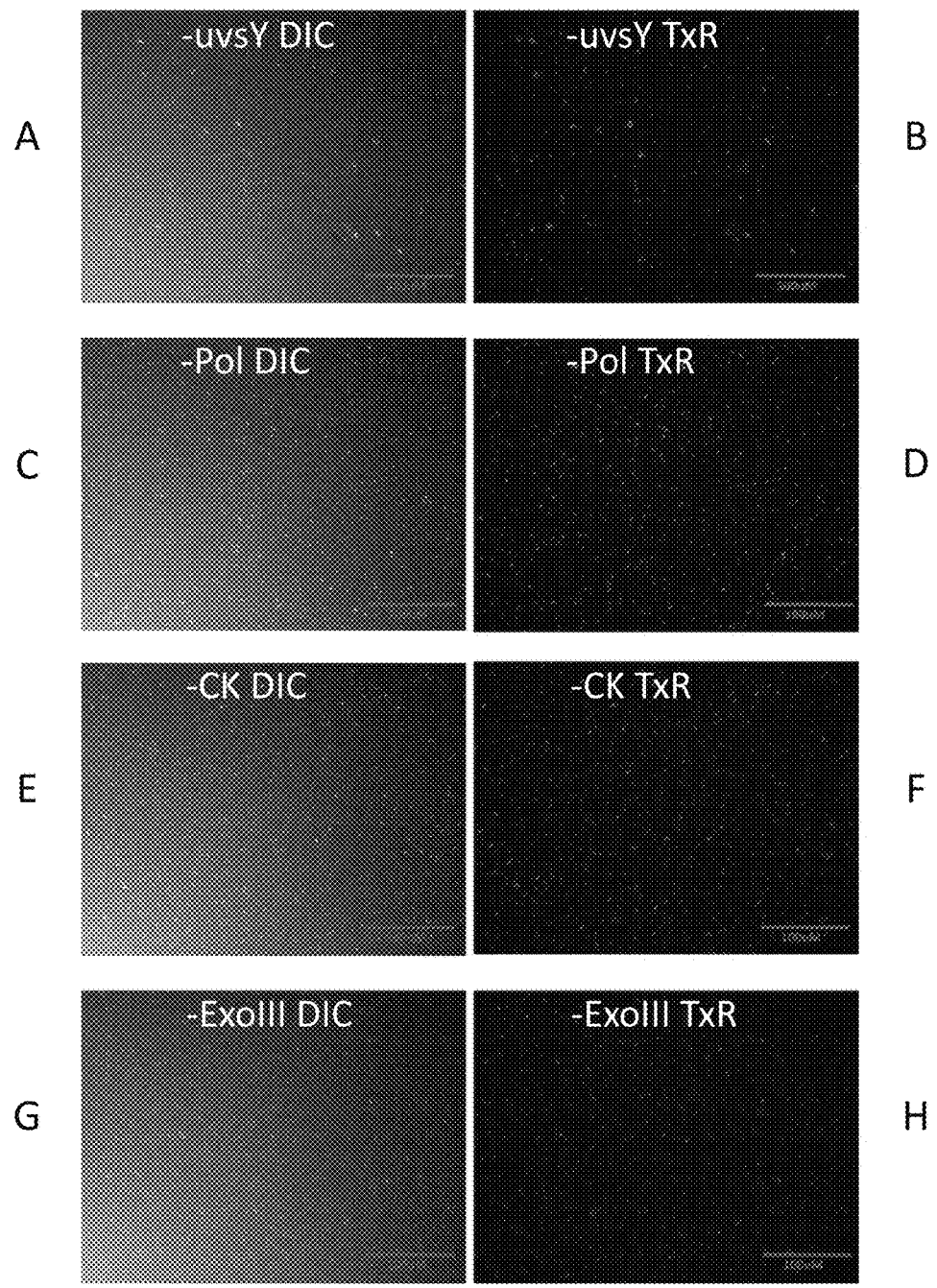
FIG. 5 shows micrographs (A-H) depicting mixtures including particles. (A) and (B) are the standard mixture as in FIGS. 4 (A) and (B), but excluding UvsY. (C) and (D) are the standard mixture excluding polymerase. (E) and (F) are the standard mixture excluding creatine kinase. (G) and (H) are the standard mixture excluding exonuclease III. (A), (C), (E), (G), DIC. (B), (D), (F), (H), fluorescence.

When all the components were present, particles formed in the mixture as described above (FIG. 4 (A-B)). Particles formed in the absence of UvsX appeared different in size from those formed in the presence of UvsX and were not easily observable by DIC (FIG. 4 (C-D)). Particles formed in the absence of gp32 appeared different in shape and size from those formed in the presence of gp32 (FIG. 4 (E-F)). Structures formed in the absence of other RPA components (UvsY, DNA polymerase, creatine kinase, or exonuclease III) appeared similar to those formed in a complete RPA reaction (FIG. 5 (A-H)). The absence of UvsY did appear to lead to a slight decrease in the number of the particles and an increase in the particle size (FIG. 5 (A-B)).

Figure 6:
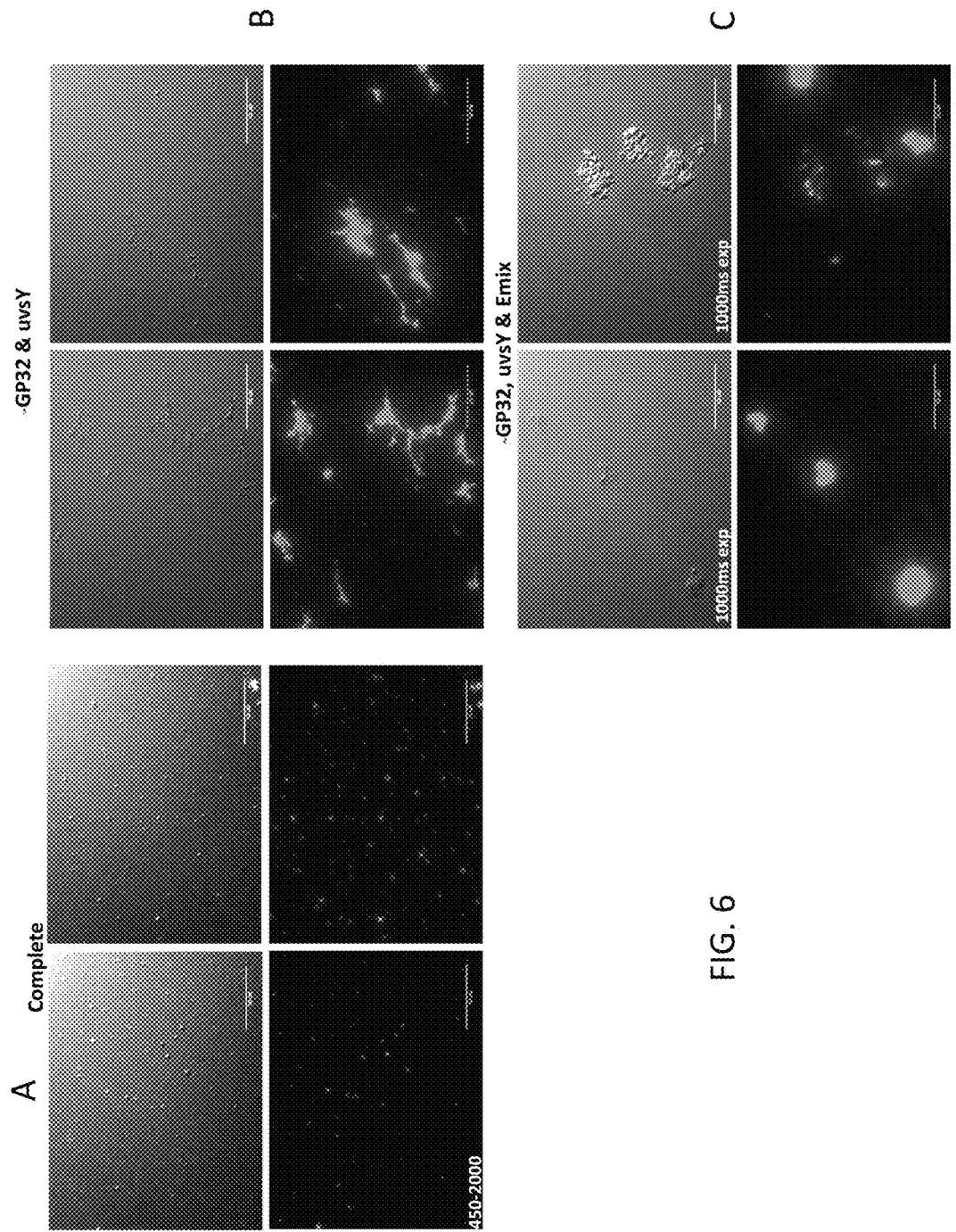
FIG. 6 shows sets of micrographs (A-C) depicting mixtures. (A), two fields showing complete mixture. (B), two fields showing complete mixture excluding gp32 and UvsY. (C), two fields showing complete mixture excluding gp32, UvsY, and Emix (50 mM Phosphocreatine, 2.5 mM ATP). For each set: top, DIC; bottom, fluorescence.

Additional mixtures were prepared excluding two or three reaction components. A control RPA mixture was prepared containing 2.96 µg Creatine Kinase, 13.1 µg Rb69 gp32, 18.8 µg T6 H66S UvsX, 5.15 µg UvsY, 8.26 µg Exonuclease III and 5.0 µg DNA Polymerase in 50 mM Tris Acetate, pH 8.3, 100 mM KOAc, 5 mM DTT, 1.2 mM dNTP mix (300 µM each of dATP, dTTP, dCTP and dGTP), 50 mM phosphocreatine, 2.5 mM ATP, 6% trehalose, 14 mM MgAc, 5.5% PEG, 120 nM M2intFAM (FAM-labeled probe 5'-tc-ctcatatccattctgTcgaatatcatcaaaagc-3'; T=carboxyfluorescein-dT; SEQ ID NO:19), 420 nM each SpaF3 (CGCTTT-GTTGATCTTTGTTGAAGTTATTTTGTTGC; SEQ ID NO:7) and SpaR10+1 (TTAAAGATGATCCAAGC-CAAAGTCCTAACGTTTTA; SEQ ID NO:8). Parallel mixtures were prepared that lacked (i) gp32 and UvsY; (ii) UvsX and UvsY; (iii) UvsX and gp32; (iv) UvsX, UvsY, and gp32; or (iv) gp32, UvsY, and Emix (phosphocreatine and ATP). No particles were observed in the mixtures lacking UvsX and at least one other component. In the mixtures lacking gp32 and UvsY, large, irregular fluorescent bodies were observed (FIG. 6 (A-C)).

This example demonstrates that exclusion of UvsX or gp32 has the largest effect on particle morphology, followed by an intermediate effect of exclusion of UvsY, with no significant effect observed on exclusion of DNA polymerase, creatine kinase, or exonuclease III. Exclusion of two or more components had increased effects.

Example 4

Separate Populations of Particles Remain Distinct when Mixed

Figure 7:
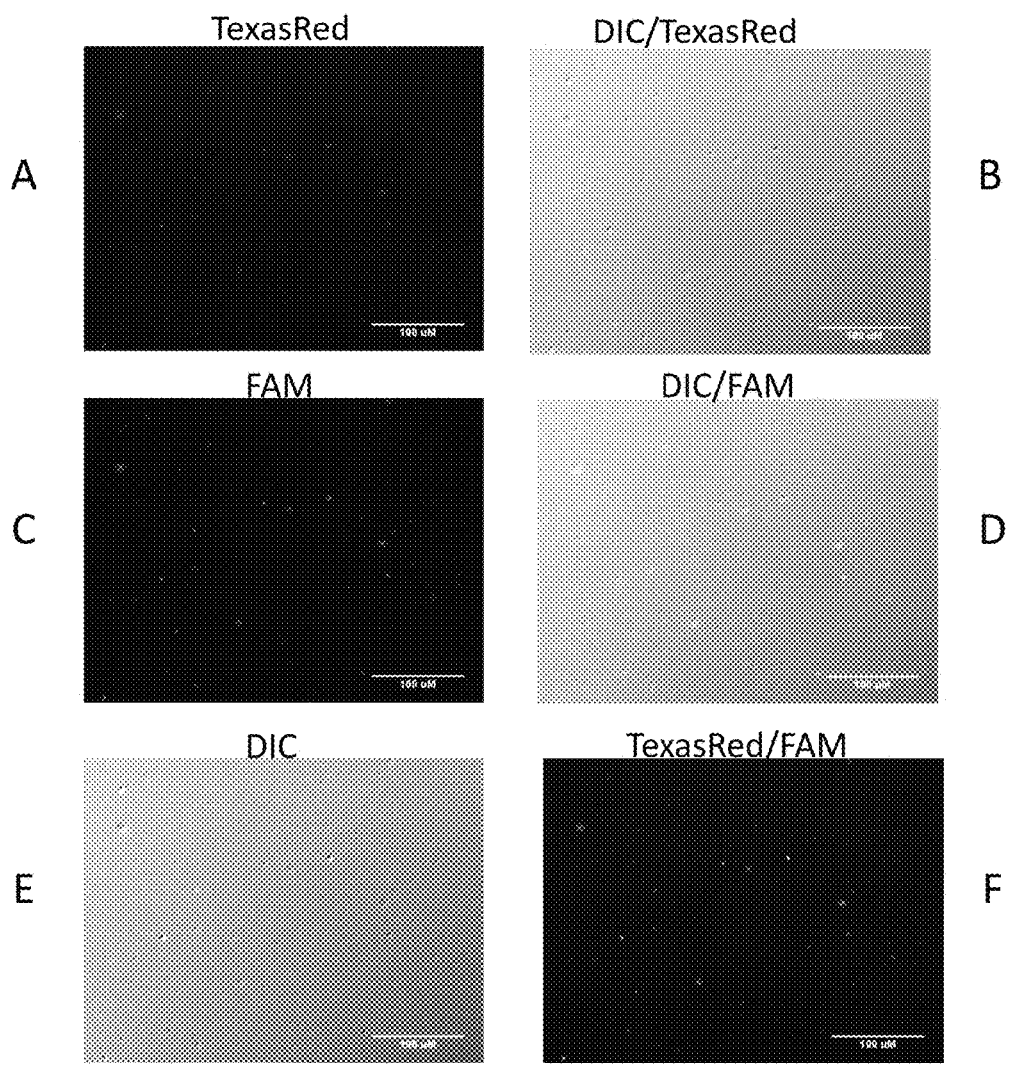
FIG. 7 shows micrographs (A-F) depicting a mixture including particles prepared with two labeled oligonucleotides. (A), Texas red fluorescence. (B), merge DIC and Texas red. (C), FAM fluorescence. (D), merge DIC and FAM. (E), DIC. (F), merge Texas red and FAM.

Two freeze-dried mixtures were prepared as described in Example 1, except that each mixture included different oligonucleotides and 18.8 µg UvsX. Reagent Mix 1 contained 296 nM SpaF3 (SEQ ID NO:7), 298 nM SpaR10+1 (SEQ ID NO:8) and 149 nM SpaProbe1 (CATCA-GCTTTTGGAGCTTGAGAGTCAT9 A8G6TTTTGA-GCTTCAC; 3' biotin, 6=BHQ-2 dT, 8=dSpacer, 9=TMR dT; SEQ ID NO:9). Reagent Mix 2 contained 299 nM MecF9-8+2 (CCCTCAAACAGGTGAA TTATTAGCACTTGT; SEQ ID NO:10), 300 nM MecR1a (CTTGTTGAGCA-GAGG TTCTTTTTTATCTTC; SEQ ID NO:11) and 150 nM MecProbe1 (ATGACGTCTAT CCATTTATGTATG-GCAFGHGQAACGAAGAATATA; 3' biotinTEG, Q=BHQ-1 dT, H=THF (abasic site mimic), F=FAM-dT; SEQ ID NO:12). Equal volumes of the two reagent mixtures were combined, and 80 µL was dispensed into 0.2-mL tubes and freeze-dried. The dried mixtures were resuspended in 46.5 µl rehydration buffer (see Example 1), 1 µL water, and 2.5 µL 280 mM MgAc. The mixture was vortexed and 10 µL was transferred to a microscope slide for imaging using DIC and fluorescence. The particles observed contained both red (TMR) and green (FAM) fluorescence, indicating that both labeled oligonucleotides were present in the particles (FIG. 7 (A-F)).

Figure 8:
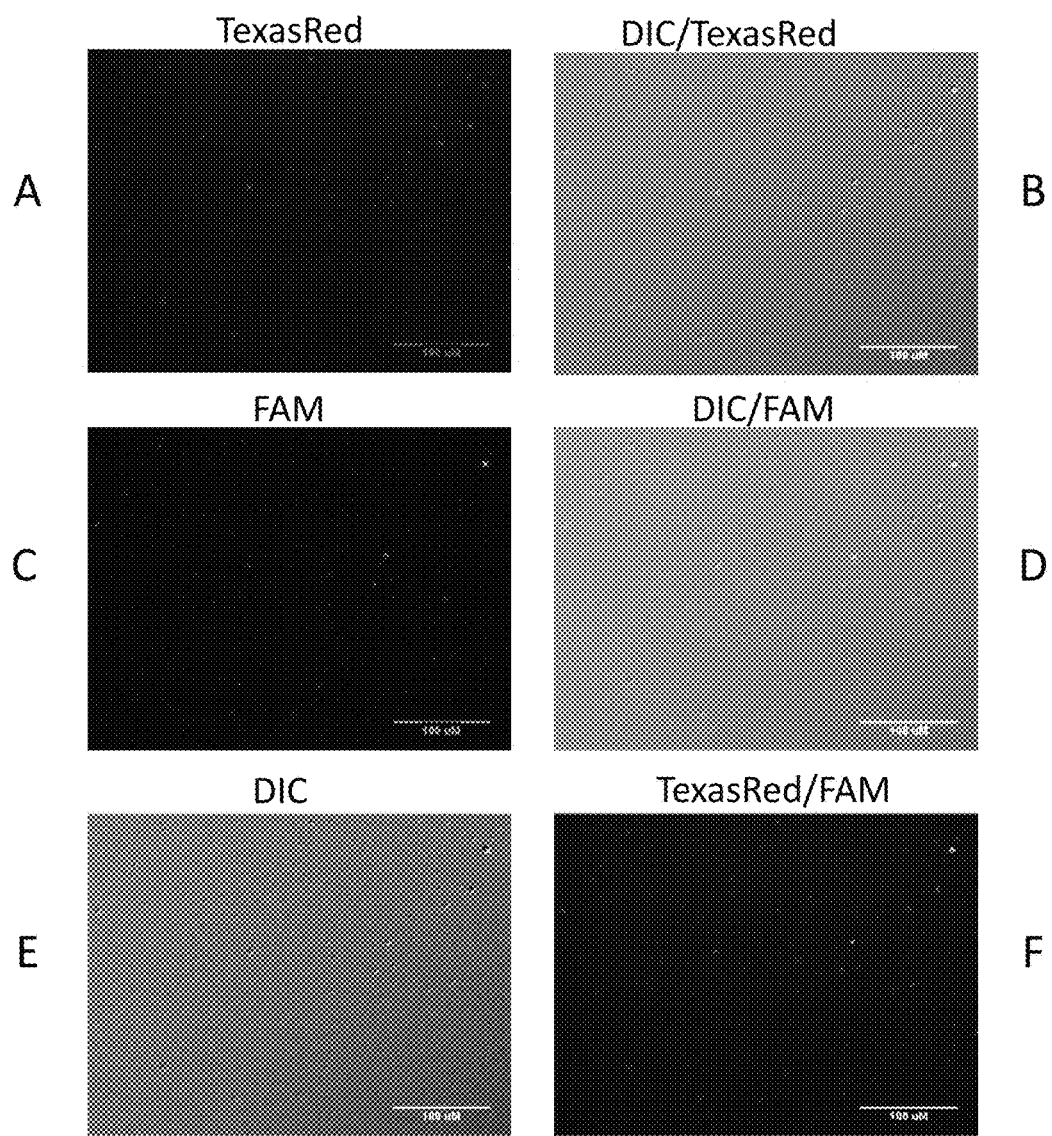
FIG. 8 shows micrographs (A-F) depicting a mixture including two sets of particles with two labeled oligonucleotides prepared independently and then mixed. (A), Texas red fluorescence. (B), merge DIC and Texas red. (C), FAM fluorescence. (D), merge DIC and FAM. (E), DIC. (F), merge Texas red and FAM.

In another experiment, two separate freeze-dried mixtures were prepared as above, one including only the TMR labeled Spa RPA probe (Reagent Mix 1, above), and the other including only the FAM-labeled MecA RPA probe (Reagent Mix 2, above). Following reconstitution, the two reconstituted mixtures were combined and imaged using DIC and fluorescence. Distinct particles that contained predominantly one fluorophore or the other were observed in the mixture (FIG. 8 (A-F)). This indicates that the particles including each probe can remain distinct from each other after mixing.

Figure 9:
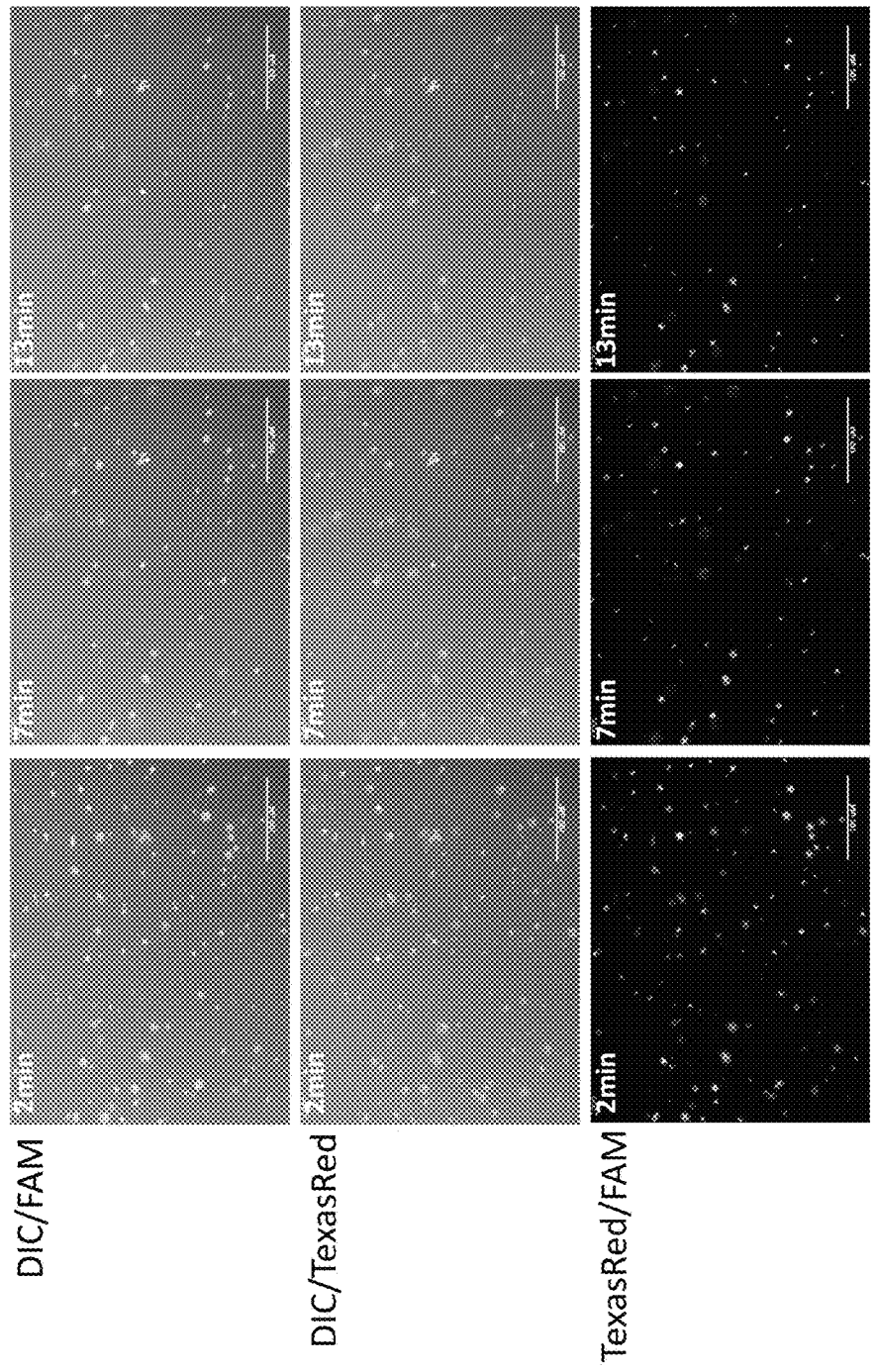
FIG. 9 is a time course of micrographs depicting particles during an amplification reaction.

To determine the stability of mixed populations of particles over time, two primer-free freeze-dried reactions were reconstituted in rehydration buffer with MgAc and oligonucleotides as below. One mixture included 30 nM HIV p2LFtexas (Texas Red labeled), 420 nM Spy1258F2 (SEQ ID NO:1, unlabeled), and 390 nM Spy1258R2 (SEQ ID NO:2, unlabeled). The other mixture included 50 nM M2intFAM oligo (SEQ ID NO:19, FAM labeled), 420 nM Spy1258F2 (SEQ ID NO:1, unlabeled), and 390 nM Spy1258R2 (SEQ ID NO:2, unlabeled). Five microliters of each mixture were pipetted onto a microscope slide and mixed, and the combination was imaged at 2, 7, and 13 minutes (FIG. 9). Images of the mixture following the 12-minute period are shown in FIG. 9. After 13 minutes, particles including predominantly Texas Red or FAM fluorescence were observable.

This example demonstrates that particles remain relatively stable in solution and can be independently labeled. This observation can be useful in monitoring two or more RPA reactions simultaneously, occurring on different particle subsets.

Example 5

RPA Reactions are Observed Localized to Particles

Figure 10:
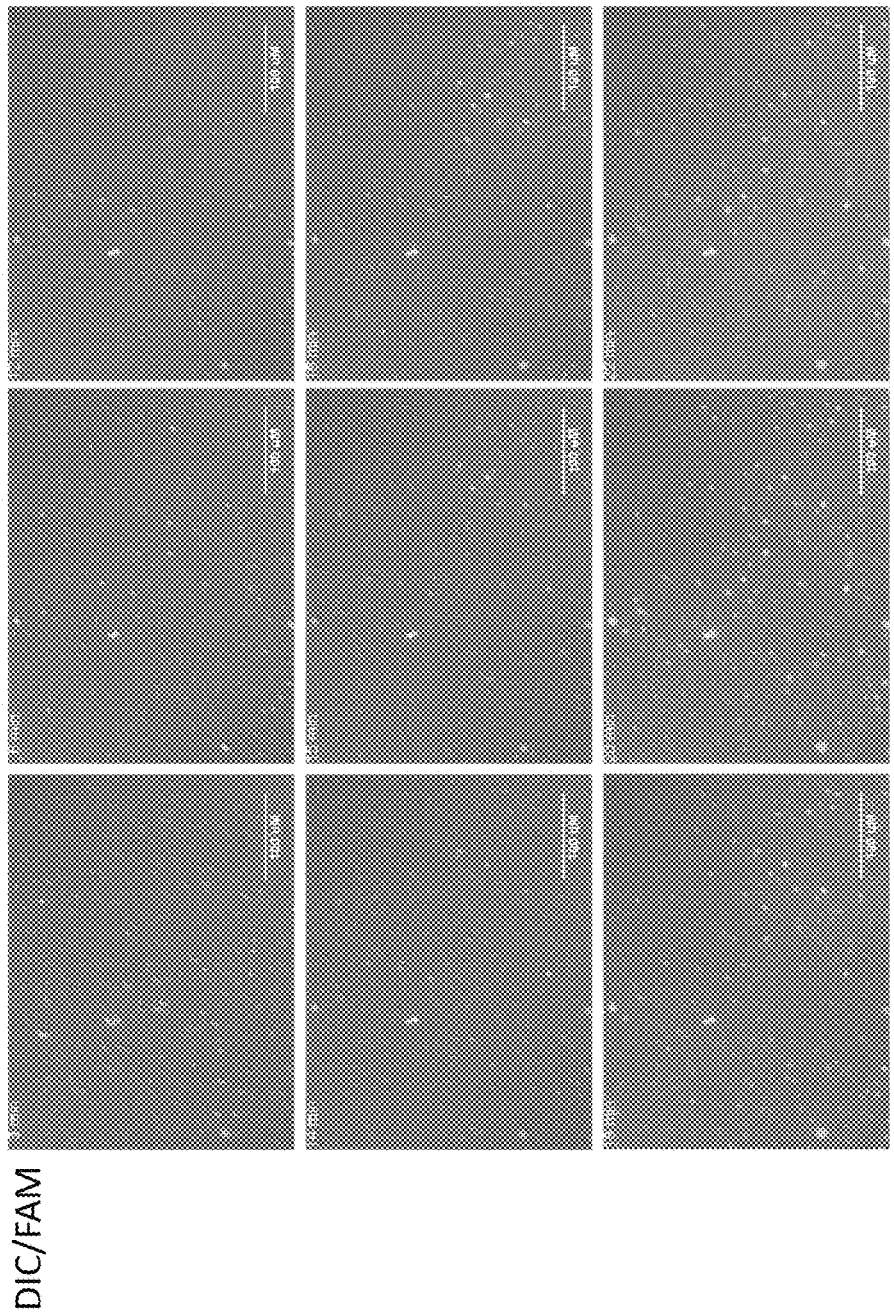
FIG. 10 is a time course of micrographs depicting particles during an amplification reaction.

Freeze dried mixtures of RPA reaction components including a FAM labeled oligonucleotide probe, as in Example 1, were reconstituted with 46.5 μl rehydration buffer, and an amplification reaction was begun by addition of 1 μL 50,000 copies/4 S. pyogenes genomic DNA and 2.5 μL 280 mM MgAc. The reaction was mixed by pipetting and transferred to a microscope slide for imaging by DIC and fluorescence starting at about 2 minutes, 40 seconds after initiation and then at 8, 12, 14, 15, 16, 18, 20, and 22 minutes (FIG. 10). An increase in fluorescence (indicating amplification) was observed, which was at least initially localized to individual particles.

Figure 11:
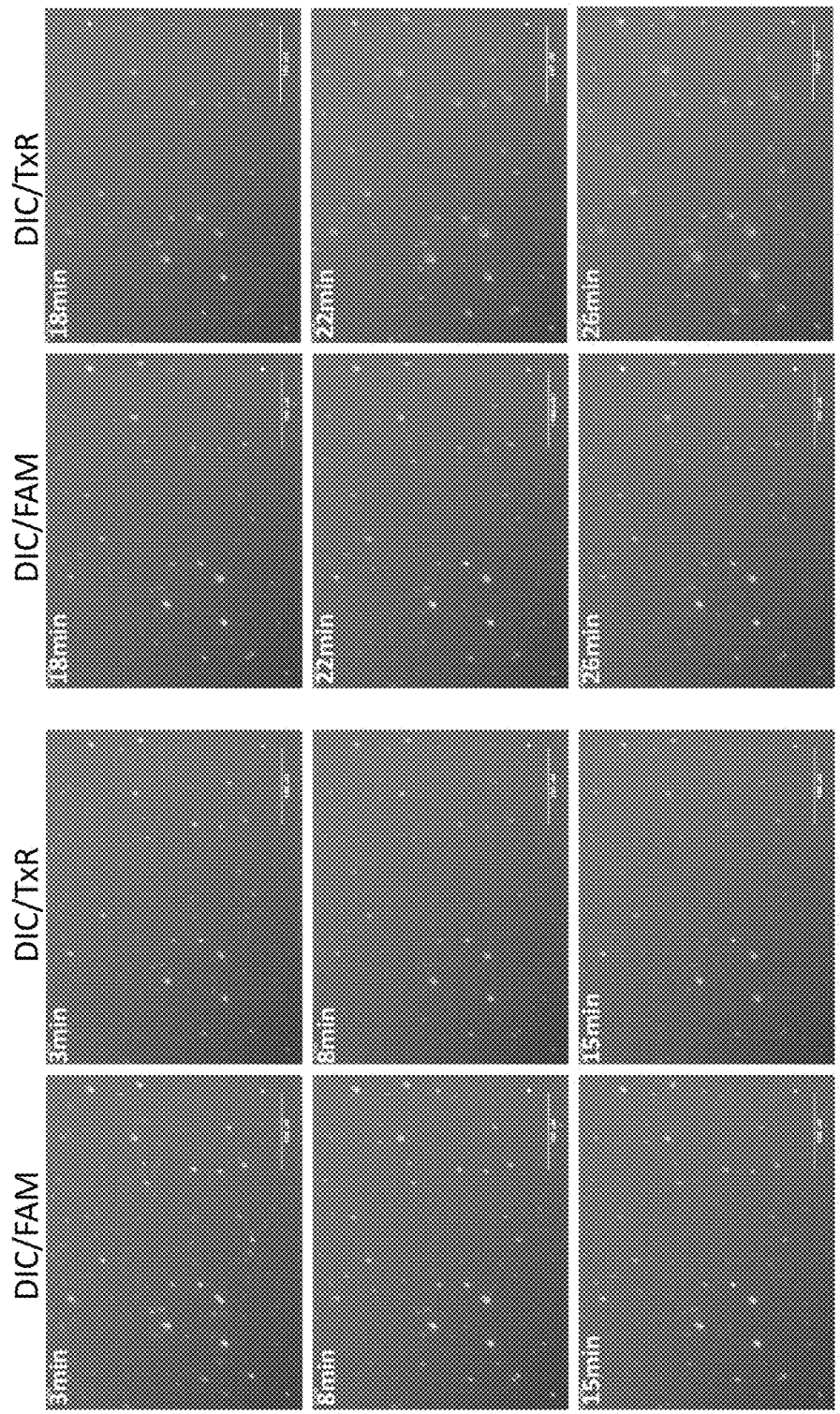
FIG. 11 is a time course of micrographs depicting particles during an amplification reaction, visualized by DIC/FAM and DIC/Texas Red.

In another experiment, freeze-dried primer-free mixtures of reaction components (prepared by mixing a 50 μl volume of 2.96 μg Creatine Kinase, 9.88 μg Rb69 gp32, 18.8 μg T6 H66S UvsX, 5.38 μg UvsY, 5.38 μg Exonuclease III and 5.34 μg DNA Polymerase in 25 mM Tris Acetate, pH 8.3, 5 mM DTT, 2.28% PEG, 5.7% trehalose, 50 mM phosphocreatine, 2.5 mM ATP, 1200 μM dNTPmix (300 μM each of dATP, dTTP, dCTP and dGTP and freeze drying in 0.2-mL tubes) were reconstituted with 29.5 μl primer-free rehydration buffer (41.7 mM Tris Acetate, 167.5 mM Potassium Acetate, 5.4% PEG, pH 8.3), 3.5 μL of 6 μM Spa F3 (SEQ ID NO:7), 3.5 μL of 6 μM Spa R10+1 (SEQ ID NO:8), 1 μL of 6 μM TMR-labeled Spa Probe 1 (SEQ ID NO:9), 1 μL of 0.6 μM M2intFAM oligo (SEQ ID NO:19, used as a fluorescent marker of particles and not involved in the RPA reaction), and 8 μL water. The reaction was initiated by addition of 1 μL 50,000 copies/4 Group A Streptococcus purified genomic template DNA and 2.5 μL 280 mM MgAc and mixing by pipette. Ten microliters of the mixture were transferred to a microscope slide, and imaging was begun about 3 minutes after initiation of the reaction. A time course of the reaction mixture at 3, 8, 15, 18, 22, and 26 minutes (FIG. 11) showed an increase in red fluorescence (indicating amplification), which was at least initially localized to individual particles.

This example demonstrates that nucleic acid amplification products can be observed colocalized with particles.

Example 6

Effects of UvsX Variants

Figure 12:
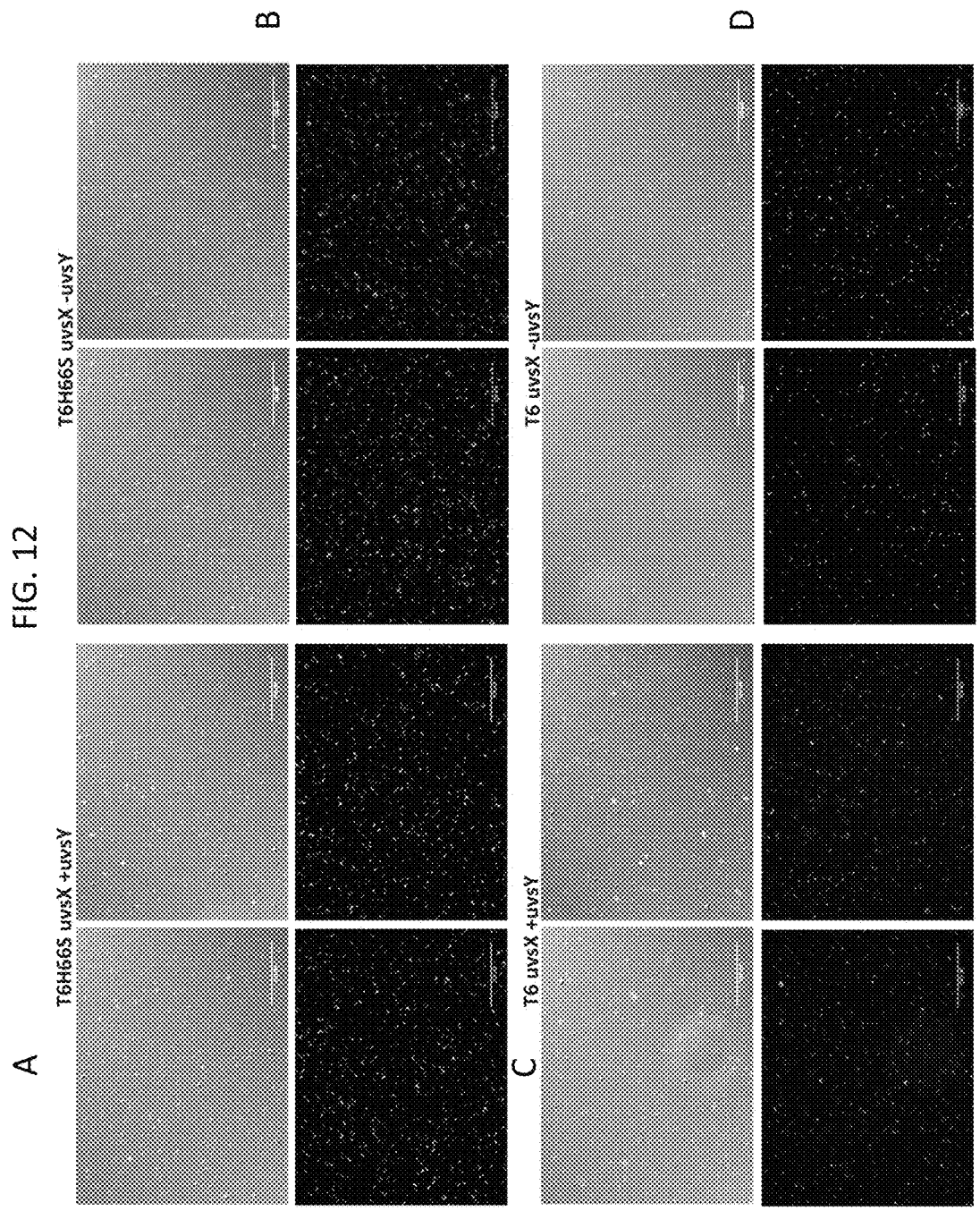
FIG. 12 shows sets of micrographs (A-D) depicting mixtures including particles at 20× magnification. (A), mixture including T6 H66S UvsX and UvsY. (B), mixture including T6 H66S UvsX without UvsY. (C), mixture including T6 UvsX and UvsY. (D), mixture including T6 UvsX without UvsY. For each set: top, DIC; bottom, fluorescence.
Figure 13:
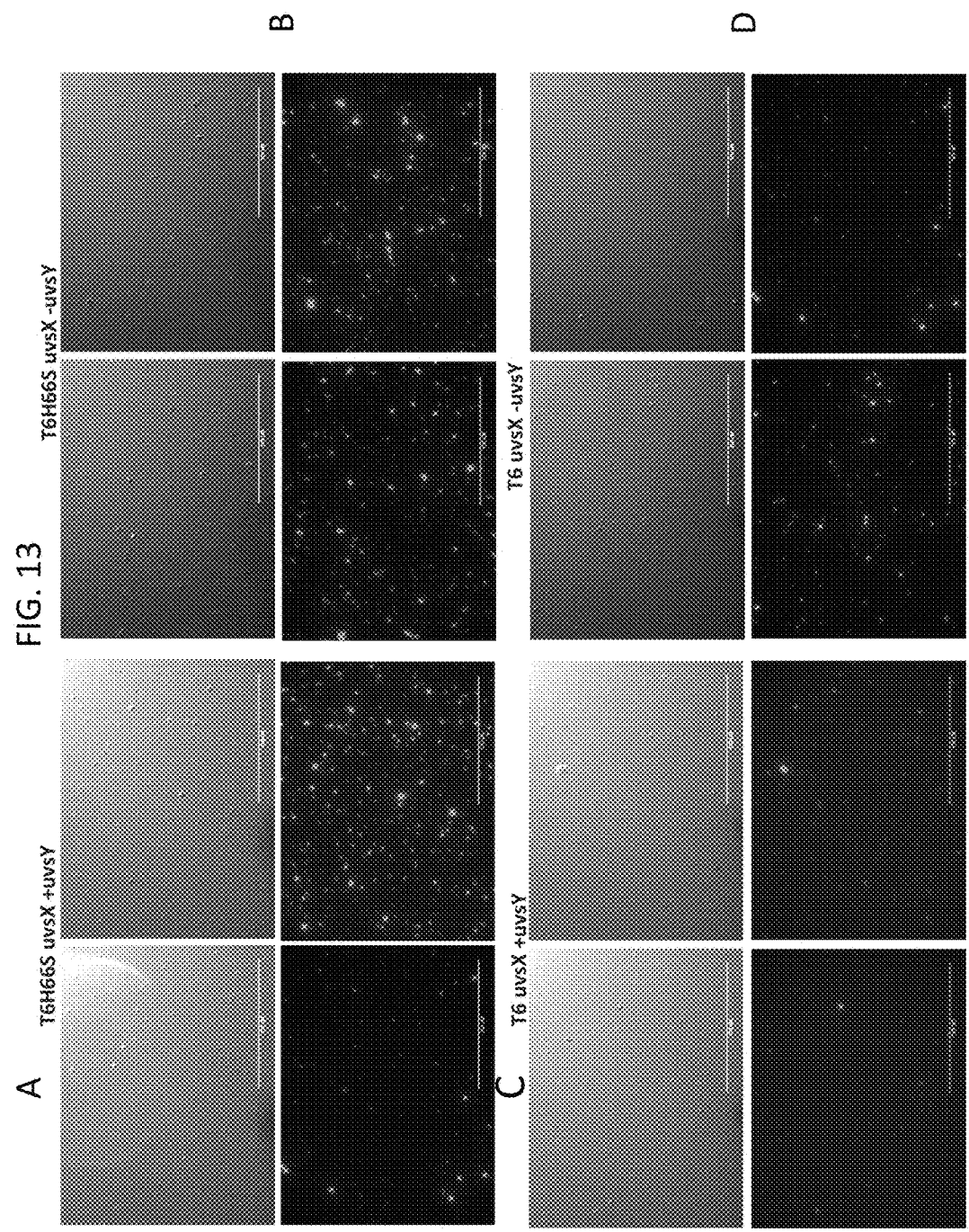
FIG. 13 shows sets of micrographs (A-D) depicting mixtures including particles at 40× magnification. (A), mixture including T6 H66S UvsX and UvsY. (B), mixture including T6 H66S UvsX without UvsY. (C), mixture including T6 UvsX and UvsY. (D), mixture including T6 UvsX without UvsY. For each set: top, DIC; bottom, fluorescence.

To investigate the effects of different UvsX variants, mixtures were set up at room temperature containing 2.96 μg Creatine Kinase, 13.1 μg Rb69 gp32, 8.26 μg Exonuclease III, 5.0 μg Polymerase in 50 mM Tris Acetate, pH 8.3, 100 mM KOAc, 5 mM DTT, 1.2 mM dNTP mix (300 μM each of dATP, dTTP, dCTP and dGTP), 50 mM phosphocreatine, 2.5 mM ATP, 6% trehalose, 14 mM MgAc, 5.5% PEG, 120 nM M2intFAM (SEQ ID NO:19), 420 nM each SpaF3 and SpaR10+1 (50 μl final volume). Four different mixtures were prepared, containing either 18.8 μg T6H66S UvsX or 17.6 μg T6 UvsX, and with or without 5.15 μg Rb69 UvsY. Ten microliters of each mixture were transferred to a microscope slide and imaged at 20× magnification about 5-20 minutes after set-up (FIG. 12 (A-D)) and also at 40× magnification about 50-60 minutes after set-up (FIG. 13 (A-D)). In general, more particles were observed in the T6H66S UvsX mixture than with T6 UvsX. Additionally the T6H66S UvsX particles were often different in shape than those with T6 UvsX, including more comet-like shapes, whereas the T6 UvsX particles were more spherical. The T6H66S UvsX mixtures lacking UvsY had has more diffuse particles and diffuse "halos" or "doughnuts" that lacked signal in the middle. With T6 UvsX the opposite effect was often observed. Without UvsY, the particles were bright small spheres, but with UvsY they were less bright and more smeary and small.

Figure 14:
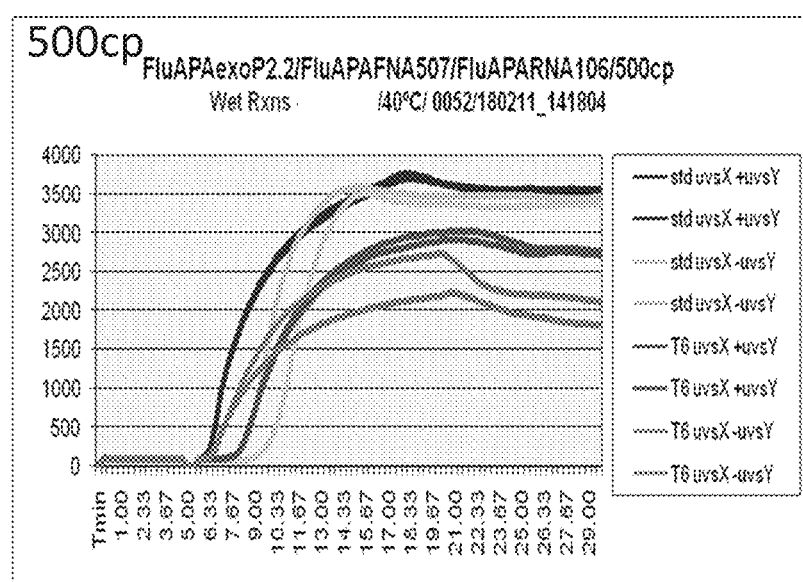
FIG. 14 shows line graphs (A-B) depicting amplification reactions in mixtures including T6 H66S UvsX and UvsY (std UvsX+UvsY), T6 H66S UvsX without UvsY (std UvsX−UvsY), T6 UvsX and UvsY (T6 UvsX+UvsY), and T6 UvsX without UvsY (T6 UvsX−UvsY). (A), 500 copies template. (B), 50 copies of template.
Figure 14:
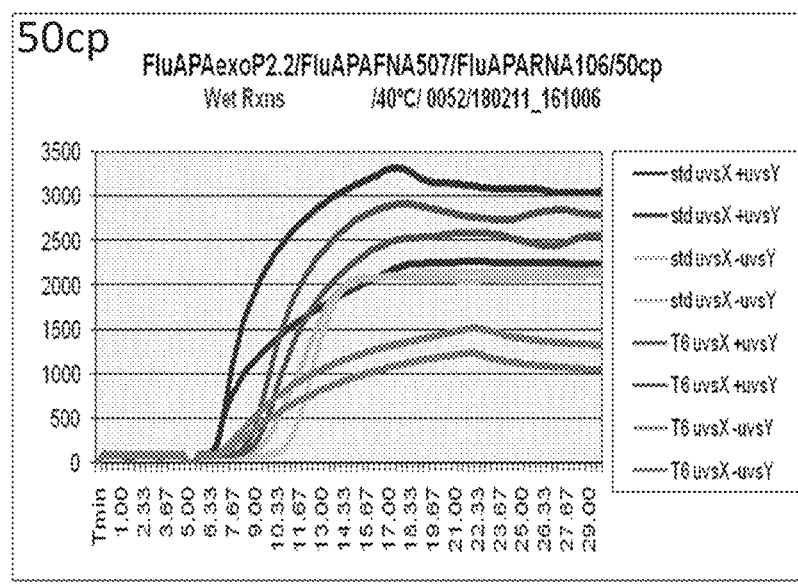
Figure 15:
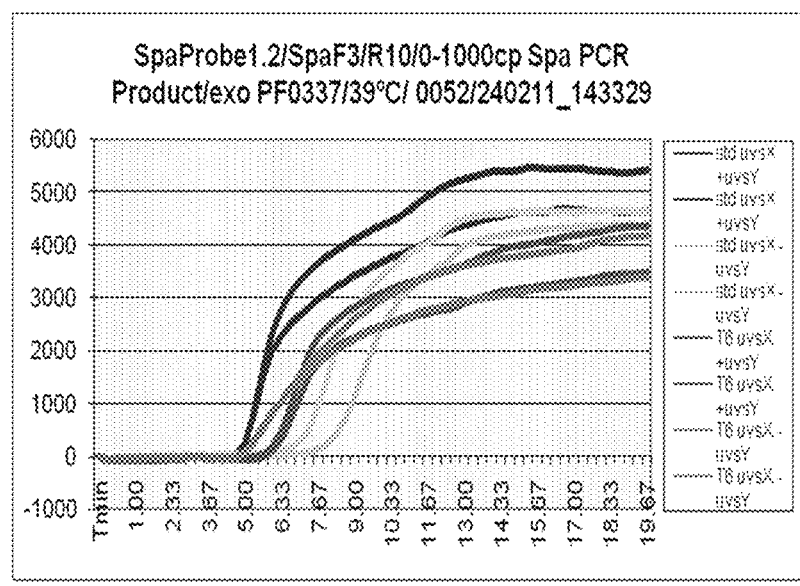
FIG. 15 is a line graph depicting amplification reactions in mixtures including T6 H66S UvsX and UvsY (std UvsX+UvsY), T6 H66S UvsX without UvsY (std UvsX−UvsY), T6 UvsX and UvsY (T6 UvsX+UvsY), and T6 UvsX without UvsY (T6 UvsX−UvsY).

The effect of UvsY on RPA reaction kinetics using T6H66S UvsX and T6 UvsX was investigated. Reactions were prepared as above, with T6H66S UvsX or T6 UvsX, and with or without Rb69 UvsY. Three separate experiments were performed using different primer sets and templates. In the first experiment, the primers were 420 nM FluA-PAFNA507 (AACCTGGGACCTTTGATCTTGGGGGGC-TATATG; SEQ ID NO:13) and FluAPARNA106 (ATGTGT-TAGGAAGGAGTTGAACCAAGAAGCATT; SEQ ID NO:14), with 120 nM probe FluAPAexoP2.2 (GATCT-TGGGGGGCTATATGAA GCAATYGAGGAGFHCQT-GATTAATGAT; F=FAM-dT, H=THF (abasic site mimic), Q=BHQ-1-dT, 3'=block c3spacer; SEQ ID NO:15). Five hundred or 50 copies of influenza A template RNA were used in each reaction. RPA reactions were assembled containing 2.96 μg Creatine Kinase, 13.1 μg Rb69 gp32, 18.8 μg T6H66S UvsX or 17.6 ug T6 UvsX, 8.26 μg Exonuclease III, 5.0 μg Polymerase, 1.79 μg Reverse Transcriptase, 5.15 μg UvsY (when present) in 50 mM Tris Acetate, pH 8.3, 100 mM KOAc, 5 mM DTT, 0.2 units/4 Ribolock™ RNAse Inhibitor (Fermentas), 1.2 mM dNTP mix (300 μM each of dATP, dTTP, dCTP and dGTP), 50 mM phosphocreatine, 2.5 mM ATP, 6% trehalose, 5.5% PEG. The above components were assembled in a 46.5 μL volume in a 0.2-mL tube, and reactions were started by addition of 2.5 µL of 280 mM MgOAc and 1 µL of 500 or 50 copies/4 influenza A template RNA. Reactions were vortexed, briefly centrifuged and transferred to a Twista instrument (ESE) and the fluorescence monitored every 20 seconds for 20 minutes at 40° C. with a mixing step (vortex and brief centrifuge) at 5 minutes. Inclusion of UvsY with T6H66S UvsX led to a delay in amplification relative to the reaction without UvsY, and the opposite was seen for T6 UvsX (FIG. 14 (A-B)). When only 50 copies of the template were present, the reactions lacking UvsY generated less signal overall (FIG. 14 (A-B)). A similar effect on reaction kinetics was observed in a second experiment using as primers 420 nM SpaF3 and SpaR10, with 120 nM SpaProbe1.2 and 1000 copies of group A *streptococcus* purified genomic template DNA (FIG. 15).

Figure 16:
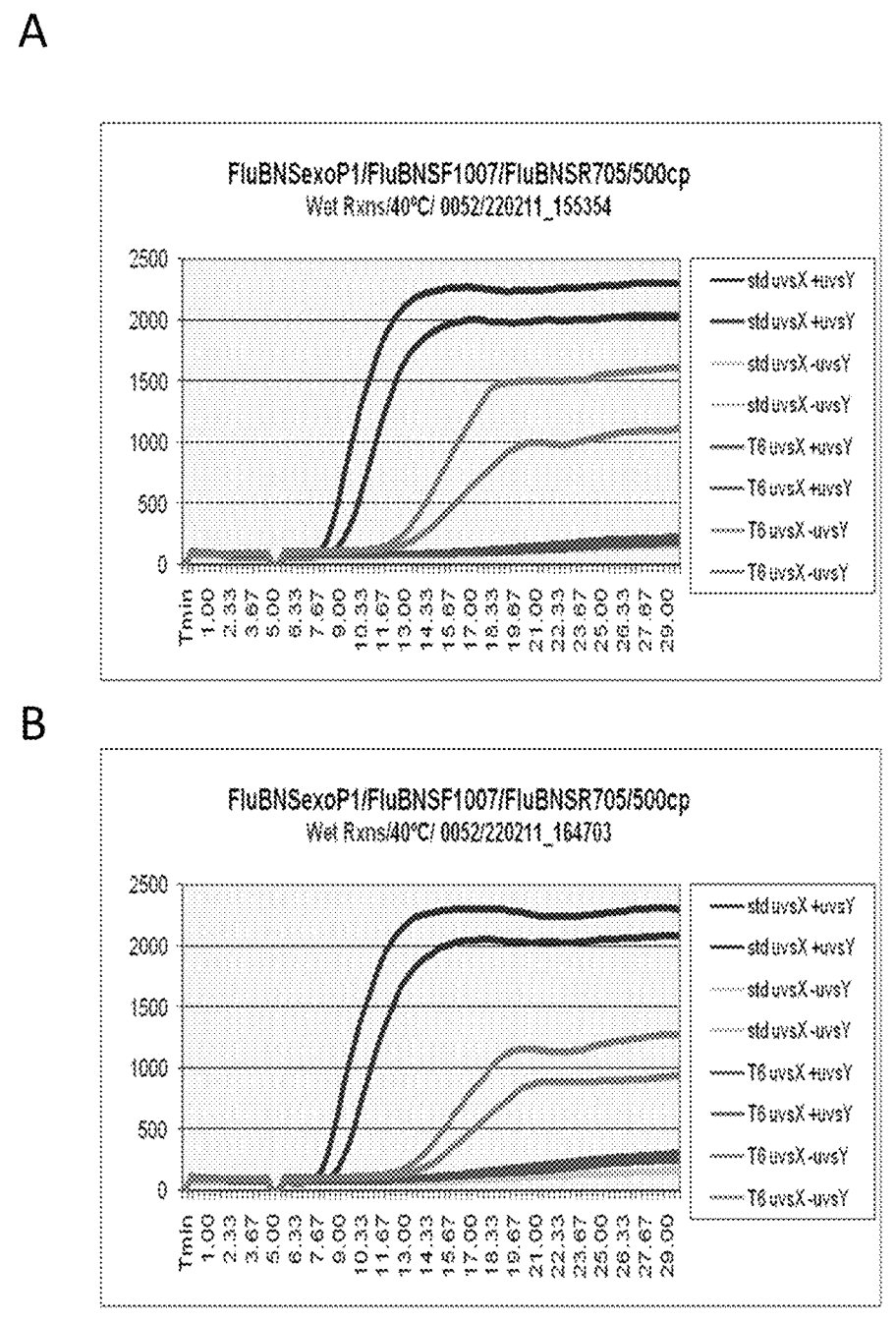

In the second experiment, the primers used were 420 nM FluBNSF1007 (CATCGGATCCTCAACTCACTCTTC-GAGCGT; SEQ ID NO:16) and FluBNSR705 (GAC-CAAATTGGGATAAGACTCCCACCGCAGTTTC; SEQ ID NO:17), with 120 nM probe FluBNSexoP1 (CATCG-GATCCTCAAYTCACTCTTCGAGCGFHTQAA TGAAGGACATTC; F=FAM-dT, H=THF (abasic site mimic), Q=BHQ-1-dT, 3'=block c3spacer; SEQ ID NO:18). Five hundred copies of PCR-amplified influenza B template DNA were used in each reaction. In these reactions, no amplification was observed with T6H66S UvsX lacking UvsY (FIG. 16 (A-B)). The opposite effect was observed with T6 UvsX (FIG. 16 (A-B)).

This example demonstrates that different UvsX variants can have different requirements for UvsY with regard to particle morphology and amplification reaction kinetics. Additionally, particle morphology appears to be correlated to the kinetics and/or progress of the amplification reaction.

Example 7

Quantification of Nucleic Acids

The methods disclosed herein can be used for the quantification of nucleic acids. In one experiment, dilutions of a template nucleic acid are combined with an RPA reaction mixture as disclosed in Example 5. The number of particles in a specified volume of the reaction that are associated with sites of nucleic acid amplification is determined at each dilution. Within a range, the number of particles associated with sites of nucleic acid amplification varies with the concentration of template nucleic acid in the reaction. For example, the number of particles associated with nucleic acid amplification can be proportional to the concentration of template nucleic acid, or the number of particles associated with nucleic acid amplification can be equivalent to the number of template nucleic acid molecules in the same volume. Using this information regarding the correlation between number of active particle and template nucleic acid concentration, the concentration of template nucleic acid in an experimental sample can be determined.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A process comprising:
    (a) providing a mixture comprising a recombinase, a DNA polymerase, a template nucleic acid, dNTPs or a mixture of dNTPs and ddNTPs, a single-stranded DNA binding protein, and one or more oligonucleotides; and
    (b) detecting particles associated with nucleic acid amplification products in the reaction mixture by observing particles or determining the number or proportion of particles associated with the nucleic acid amplification products in the reaction mixture.

2. The process of claim 1, wherein the mixture comprises a crowding agent.

3. The process of claim 2, wherein the crowding agent comprises polyethylene glycol, polyvinyl alcohol, dextran and/or Ficoll.

4. The process of claim 2, wherein the crowding agent comprises polyethylene glycol.

5. The process of claim 3, wherein the polyethylene glycol is selected from the group consisting of PEG1450, PEG3000, PEG8000, PEG10000, PEG14000, PEG15000, PEG20000, PEG250000, PEG30000, PEG35000, PEG40000, PEG compound with molecular weight between 15,000 and 20,000 daltons, and combinations thereof.

6. The process of claim 2, wherein the crowding agent is present in the mixture at a concentration between 1 to 12% by weight or by volume of the mixture.

7. The process of claim 1, wherein the recombinase comprises a RecA or UvsX protein.

8. The process of claim 1, wherein the single-stranded DNA binding protein (SSB) comprises a prokaryotic SSB protein or a myoviridae gp32 protein.

9. The process of claim 1, wherein at least one of the one or more oligonucleotides comprises a detectable label.

10. The process of claim 1, wherein the particles comprise one or more of the recombinase, the single-strand binding protein, and at least one of the one or more oligonucleotides.

11. The process of claim 1, wherein the mixture further comprises one or more of: a recombinase loading protein, a reducing agent, creatine kinase, a nuclease, a nucleic acid probe, and a reverse transcriptase.

12. The process of claim 1, wherein the particles are about 1-10 μm in size.

13. The process of claim 1, wherein detecting particles in the mixture comprises the use of microscopy.

14. The process of claim 1, wherein detecting particles in the mixture comprises the use of a lab-on-a-chip device.

15. The process of claim 1, wherein detecting particles in the mixture comprises the use of flow cytometry.

16. The process of claim 1, wherein the particles are about 0.5-20 μm in size.

17. The process of claim 1, wherein the particles are detected using fluorescence from the particles.

18. The process of claim 1, wherein the particles are detected without using fluorescence from the particles.

19. The process of claim 1, wherein the particles comprise a first subset of particles and a second subset of particles, the first subset of particles is detected using fluorescence from the first subset of particles, and the second subset of particles are-detected without using fluorescence from the second subset of particles.

* * * * *

UNITED STATES PATENT AND TRADEMARK OFFICE
CERTIFICATE OF CORRECTION

PATENT NO. : 9,719,132 B2  
APPLICATION NO. : 14/841203  
DATED : August 1, 2017  
INVENTOR(S) : Niall A. Armes, Olaf Piepenburg and Catherine Jean Greenwood Page 1 of 1

It is certified that error appears in the above-identified patent and that said Letters Patent is hereby corrected as shown below:

In the Specification

Column 1, Line 13, delete "61/472,929," and insert -- 61/472,919, --

In the Claims

Column 29, Line 50, Claim 5, delete "PEG250000," and insert -- PEG25000, --

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 19

<210> SEQ ID NO 1
<211> LENGTH: 34
<212> TYPE: DNA
<213> ORGANISM: Artificial Sequence
<220> FEATURE:
<223> OTHER INFORMATION: amplification primer

<400> SEQUENCE: 1
cacagacact cgacaagtcc tcaatcaaac cttg                                 34

<210> SEQ ID NO 2
<211> LENGTH: 34
<212> TYPE: DNA
<213> ORGANISM: Artificial Sequence
<220> FEATURE:
<223> OTHER INFORMATION: amplification primer

<400> SEQUENCE: 2
cagaaatcct tgatgagttg cggaaatttg aggt                                 34

<210> SEQ ID NO 3
<211> LENGTH: 49
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: 31
<223> OTHER INFORMATION: n=BHQ-1-dT
<220> FEATURE:
```

```
<221> NAME/KEY: misc_feature
<222> LOCATION: 33
<223> OTHER INFORMATION: n=THF (abasic site mimic)
<220> FEATURE:
<221> NAME/KEY: misc_feature
<222> LOCATION: 34
<223> OTHER INFORMATION: n=FAM-dT

<400> SEQUENCE: 3
ccttgtccta ccttatagaa catagagaat ntnnaaccgc actcgctac            49

<210> SEQ ID NO 4
<211> LENGTH: 44
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 31
<223> OTHER INFORMATION: n=dSpacer

<400> SEQUENCE: 4
agaattacaa aaacaaatta caaaaattca naattttcgg gttt                 44

<210> SEQ ID NO 5
<211> LENGTH: 34
<212> TYPE: DNA
<213> ORGANISM: Artificial Sequence
<220> FEATURE:
<223> OTHER INFORMATION: amplification primer

<400> SEQUENCE: 5
cacagacact cgacaagtcc tcaatcaaac cttg                            34

<210> SEQ ID NO 6
<211> LENGTH: 34
<212> TYPE: DNA
<213> ORGANISM: Artificial Sequence
<220> FEATURE:
<223> OTHER INFORMATION: amplification primer

<400> SEQUENCE: 6
cagaaatcct tgatgagttg cggaaatttg aggt                            34

<210> SEQ ID NO 7
<211> LENGTH: 35
<212> TYPE: DNA
<213> ORGANISM: Artificial Sequence
<220> FEATURE:
<223> OTHER INFORMATION: amplification primer

<400> SEQUENCE: 7
cgctttgttg atctttgttg aagttatttt gttgc                           35

<210> SEQ ID NO 8
<211> LENGTH: 35
<212> TYPE: DNA
<213> ORGANISM: Artificial Sequence
<220> FEATURE:
<223> OTHER INFORMATION: amplification primer

<400> SEQUENCE: 8
ttaaagatga tccaagccaa agtcctaacg tttta                           35

<210> SEQ ID NO 9
<211> LENGTH: 45
```

```
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: 28
<223> OTHER INFORMATION: n=TMR dT
<220> FEATURE:
<221> NAME/KEY: misc_feature
<222> LOCATION: 30
<223> OTHER INFORMATION: n=dSpacer
<220> FEATURE:
<221> NAME/KEY: misc_feature
<222> LOCATION: 32
<223> OTHER INFORMATION: n=BHQ-2 dT

<400> SEQUENCE: 9
catcagcttt tggagcttga gagtcatnan gnttttgagc ttcac                45

<210> SEQ ID NO 10
<211> LENGTH: 30
<212> TYPE: DNA
<213> ORGANISM: Artificial Sequence
<220> FEATURE:
<223> OTHER INFORMATION: amplification primer

<400> SEQUENCE: 10
ccctcaaaca ggtgaattat tagcacttgt                                 30

<210> SEQ ID NO 11
<211> LENGTH: 30
<212> TYPE: DNA
<213> ORGANISM: Artificial Sequence
<220> FEATURE:
<223> OTHER INFORMATION: amplification primer

<400> SEQUENCE: 11
cttgttgagc agaggttctt ttttatcttc                                 30

<210> SEQ ID NO 12
<211> LENGTH: 45
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: 28
<223> OTHER INFORMATION: n=FAM-dT
<220> FEATURE:
<221> NAME/KEY: misc_feature
<222> LOCATION: 30
<223> OTHER INFORMATION: n=THF (abasic site mimic)
<220> FEATURE:
<221> NAME/KEY: misc_feature
<222> LOCATION: 32
<223> OTHER INFORMATION: n=BHQ-1 dT

<400> SEQUENCE: 12
atgacgtcta tccatttatg tatggcangn gnaacgaaga atata                45

<210> SEQ ID NO 13
<211> LENGTH: 33
<212> TYPE: DNA
<213> ORGANISM: Artificial Sequence
<220> FEATURE:
<223> OTHER INFORMATION: amplification primer

<400> SEQUENCE: 13
```
aacctgggac ctttgatctt gggggggctat atg                            33

<210> SEQ ID NO 14
<211> LENGTH: 33
<212> TYPE: DNA
<213> ORGANISM: Artificial Sequence
<220> FEATURE:
<223> OTHER INFORMATION: amplification primer

<400> SEQUENCE: 14
atgtgttagg aaggagttga accaagaagc att                             33

<210> SEQ ID NO 15
<211> LENGTH: 48
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: 27
<223> OTHER INFORMATION: n=a,g,c,t
<220> FEATURE:
<221> NAME/KEY: misc_feature
<222> LOCATION: 34
<223> OTHER INFORMATION: n=FAM-dT
<220> FEATURE:
<221> NAME/KEY: misc_feature
<222> LOCATION: 35
<223> OTHER INFORMATION: n=THF (abasic site mimic)
<220> FEATURE:
<221> NAME/KEY: misc_feature
<222> LOCATION: 37
<223> OTHER INFORMATION: n=BHQ-1-dT

<400> SEQUENCE: 15
gatcttgggg ggctatatga agcaatngag gagnncntga ttaatgat             48

<210> SEQ ID NO 16
<211> LENGTH: 30
<212> TYPE: DNA
<213> ORGANISM: Artificial Sequence
<220> FEATURE:
<223> OTHER INFORMATION: amplification primer

<400> SEQUENCE: 16
catcggatcc tcaactcact cttcgagcgt                                 30

<210> SEQ ID NO 17
<211> LENGTH: 34
<212> TYPE: DNA
<213> ORGANISM: Artificial Sequence
<220> FEATURE:
<223> OTHER INFORMATION: amplification primer

<400> SEQUENCE: 17
gaccaaattg ggataagact cccaccgcag tttc                            34

<210> SEQ ID NO 18
<211> LENGTH: 47
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: 15
<223> OTHER INFORMATION: n=a,c,g,t
<220> FEATURE:
<221> NAME/KEY: misc_feature

```
<222> LOCATION: 30
<223> OTHER INFORMATION: n=FAM-dT
<220> FEATURE:
<221> NAME/KEY: misc_feature
<222> LOCATION: 31
<223> OTHER INFORMATION: n=THF (abasic site mimic)
<220> FEATURE:
<221> NAME/KEY: misc_feature
<222> LOCATION: 33
<223> OTHER INFORMATION: n=BHQ-1-dT

<400> SEQUENCE: 18
catcggatcc tcaantcact cttcgagcgn ntnaatgaag gacattc                47

<210> SEQ ID NO 19
<211> LENGTH: 35
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 18
<223> OTHER INFORMATION: n=carboxyfluorescein-dT

<400> SEQUENCE: 19
tcctcatatc cattctgncg aatatcatca aaagc                             35
```